US012708338B2

(12) United States Patent
Friedrich et al.

(10) Patent No.: US 12,708,338 B2
(45) Date of Patent: Aug. 18, 2026

(54) TECHNIQUE FOR COMPENSATING AN X-RAY GRID SHADOW USING AN ACTUATOR SYSTEM

(71) Applicant: Siemens Healthineers AG, Forchheim (DE)

(72) Inventors: Stefan Friedrich, Stegaurach (DE); Philipp Bernhardt, Forchheim (DE)

(73) Assignee: Siemens Healthineers AG, Forchheim (DE)

( * ) Notice: Subject to any disclaimer, the term of this patent is extended or adjusted under 35 U.S.C. 154(b) by 152 days.

(21) Appl. No.: 18/884,582

(22) Filed: Sep. 13, 2024

(65) Prior Publication Data

US 2025/0090124 A1 Mar. 20, 2025

(30) Foreign Application Priority Data

Sep. 15, 2023 (DE) ..................... 10 2023 208 969.6

(51) Int. Cl.
*A61B 6/00* (2024.01)
*A61B 6/58* (2024.01)

(52) U.S. Cl.
CPC ............. *A61B 6/54* (2013.01); *A61B 6/4441* (2013.01); *A61B 6/483* (2013.01); *A61B 6/587* (2013.01)

(58) Field of Classification Search
CPC .... A61B 6/00; A61B 6/14; A61B 6/54; A61B 6/4441; A61B 6/483; A61B 6/587;
(Continued)

(56) References Cited

U.S. PATENT DOCUMENTS

2016/0183909 A1 6/2016 Mehendale
2017/0358379 A1 12/2017 Kraemer
(Continued)

FOREIGN PATENT DOCUMENTS

DE 102016210529 A1 12/2017
EP 3692918 A1 8/2020
(Continued)

OTHER PUBLICATIONS

Schulman, John, et al. "Proximal Policy Optimization Algorithms." arXiv preprint arXiv:1707.06347 (2017) pp. 1-12.
(Continued)

*Primary Examiner* — Courtney D Thomas
(74) *Attorney, Agent, or Firm* — Lempia Summerfield Katz LLC

(57) ABSTRACT

A technique for controlling a compensation actuator system for compensating a shadow of an X-ray scattered radiation absorption grid in an X-ray image recorded with a pivotably mounted X-ray device, for example in real time, includes a method with a step of receiving motion state data indicative of a motion state of an X-ray device. The X-ray device is mounted on a pivotable arm. The motion state is assigned to a time of recording of an X-ray image by the X-ray device. A quality measure of the X-ray image with respect to a shadow of an X-ray scattered radiation absorption grid, which is arranged on the detector of the X-ray device, is determined. A control signal for a compensation actuator system for adjusting the position of the X-ray scattered radiation absorption grid is determined depending on the received motion state data and depending on the determined quality measure. Determining the control signal comprises optimizing the quality measure. The control signal determined is output to the compensation actuator system in order
(Continued)

to compensate the shadow of the X-ray scattered radiation absorption grid.

16 Claims, 10 Drawing Sheets

(58) Field of Classification Search
CPC ....... A61B 6/06; A61B 6/4291; A61B 6/5282; A61B 6/547; G01T 1/20; G01T 1/29; G06T 7/00; G06T 5/00; G05B 13/02; G05D 3/00
See application file for complete search history.

(56) References Cited

U.S. PATENT DOCUMENTS

2020/0258222 A1 8/2020 Bernhardt
2021/0007700 A1* 1/2021 Withagen ............... A61B 6/587
2021/0338183 A1 11/2021 Elenbaas
2023/0117579 A1 4/2023 Steadman Booker

FOREIGN PATENT DOCUMENTS

EP 4523628 A1 3/2025
KR 20160086211 A 7/2016

OTHER PUBLICATIONS

Singh, Avi, et al. "End-to-End Robotic Reinforcement Learning without Reward Engineering." University of California, Berkeley (2019) pp. 1-10.
Bristow, Douglas A., Marina Tharayil, and Andrew G. Alleyne. "A Survey of Iterative Learning Control." IEEE Control Systems Magazine 26.3 (2006): pp. 96-114.
Shen, Dong. "Iterative Learning Control with Incomplete Information: A Survey." IEEE/CAA Journal of Automatica Sinica 5.5 (2018): pp. 885-901.
Strijbosch, Nard, and Tom Oomen. "Iterative Learning Control for Intermittently Sampled Data: Monotonic Convergence, Design, and Applications." Automatica 139 (2022): 110171. pp. 1-12.
Abelli, Andrea, et al. "Adaptive Inverse Control Using Kernel Identification." 2012 American Control Conference (ACC). IEEE, 2012. pp. 202-207.
Santamaria, Ignatio. "Kernel Adaptive Filtering: A Comprehensive Introduction" [Book Review]. IEEE Computational Intelligence Magazine 5.3 (2010): pp. 52-55.
Friedrich, Stefan R., Michael Schreibauer, and Martin Buss. "Least-Squares Policy Iteration Algorithms for Robotics: Online, Continuous, and Automatic." Engineering Applications of Artificial Intelligence 83 (2019): pp. 72-84.
Engel, Yaakov, Shie Mannor, and Ron Meir. "The Kernel Recursive Least-Squares Algorithm." IEEE Transactions on Signal Processing 52.8 (2004): pp. 2275-2285.
Van Vaerenbergh, Steven, Miguel Lázaro-Gredilla, and Ignacio Santamaría. "Kernel Recursive Least-Squares Tracker for Time-Varying Regression." IEEE Transactions on Neural Networks and Learning Systems 23.8 (2012): pp. 1313-1326.
Zhao, Songlin, et al. "Fixed Budget Quantized Kernel Least-Mean-Square Algorithm." Signal Processing 93.9 (2013): pp. 2759-2770.
Zhang, Yunzhi, et al. "Asynchronous Methods for Model-Based Reinforcement Learning." arXiv preprint arXiv:1910.12453 (2019) pp. 1-10.
Van Vaerenbergh, Steven, and Ignacio Santamaría. "A Comparative Study of Kernel Adaptive Filtering Algorithms." University of Cantabria, (2013) pp. 1-6.
Geering, Hans P., and C. Roduner. "Design of Robust Controllers with the H-method." Bulletin des Schweizerischen Elektrotechnischen Vereins 90.3 (1999): pp. 55-58.
Schroder, Dierk, and Martin Buss. "Intelligent Methods—System Identification and Closed-loop Control of Non-linear Systems". Springer Berlin Heidelberg, (2017) with English translation.

* cited by examiner

200

202

208

210

212

204

206

214

216

302
304
312
312
308
306
310

302
304
314
314
308
316
306
310

S102
S106
S108
614
S110
602
q_d,\dot{q}_d
q,\dot{q}
604
y_d
606
608
610
612
S104
c_i,c_x,c_y
616

S102
S106
S108
614
S110
602
q_d,\dot{q}_d
q,\dot{q}
605
y_d
606
608
610
612
S104
618

S106
S108
614
S110
605
y_d
q_d,\dot{q}_d
606
608
610
612
S104
618
620
S102

TECHNIQUE FOR COMPENSATING AN X-RAY GRID SHADOW USING AN ACTUATOR SYSTEM

CROSS REFERENCE TO RELATED APPLICATIONS

This application claims the benefit DE 10 2023 208 969.6 filed on Sep. 15, 2023, which is hereby incorporated by reference in its entirety.

FIELD

Embodiments relate to a technique for controlling a compensation actuator system for compensating a shadow of an X-ray scattered radiation absorption grid in an X-ray image recorded with a pivotably mounted X-ray device, for example in real time.

BACKGROUND

To generate an X-ray image, X-ray scattered radiation absorption grids (also: referred to as X-ray grids, scattered radiation absorption grids and/or scattered radiation rasters) are usually introduced into the beam path between the X-ray emitter (also: X-ray source and/or emitter) and the X-ray detector (detector for short). Thus, the scattered radiation is filtered out with a scattered radiation raster in front of the image receiver in order to increase image quality. New methods, for example additive methods, provide the production of scattered radiation rasters with high aspect ratios (and/or a high height of the structure relative to the structure period), so-called super rasters, "smart grids" or focused rasters.

With focused rasters (also: "smart grids"), the slats are not only higher than for conventional scattered radiation rasters in order to achieve better filtering, but also directed in the direction of the center point of the emitter in order to obtain a large proportion of useful radiation.

However, the new types of focused rasters (which may also be referred to as X-ray grids or grids for short) are not readily usable in conventional angiography systems, because movements caused by elastic deformation in the device or the gantry cause the focal point of the X-ray emitter to migrate strongly, resulting in shadowing and visible artifacts in the imaging.

Conventional methods for active tracking of the X-ray grid use a calculation of the control commands for the correction drives based on an elastostatic model of a C-arm. However, the tracking obtained in this way is not precise enough to ensure good image quality of an X-ray recording.

BRIEF SUMMARY AND DESCRIPTION

The scope of the present disclosure is defined solely by the claims and is not affected to any degree by the statements within this summary. The present embodiments may obviate one or more of the drawbacks or limitations in the related art. Independent of the grammatical term usage, individuals with male, female or other gender identities are included within the term.

Embodiments provide a reliable solution for improved image quality, for example in real time, of an X-ray recording accompanied by a reduced radiation dose.

This object is achieved by a method for controlling a compensation actuator system for compensating a shadow of an X-ray scattered radiation absorption grid in an X-ray image recorded with a pivotably mounted X-ray device, for example in real time, by a computing apparatus, by a system including the computing apparatus, by a computer program (and/or a computer program product) and by a computer-readable storage medium.

According to one aspect, a method (for example a computer-implemented method) for controlling a compensation actuator system for compensating a shadow of an X-ray scattered radiation absorption grid in an X-ray image recorded with a pivotably mounted X-ray device, for example in real time, is provided.

The method includes a step of receiving (for example target and/or actual) motion state data indicative of a motion state of an X-ray device. The X-ray device is mounted on a pivotable arm. The motion state is assigned to a time of recording of an X-ray image by the X-ray device. The method further includes a step of determining a quality measure of the X-ray image with respect to a shadow of an X-ray scattered radiation absorption grid, which is arranged on the detector of the X-ray device. The method further includes a step of determining a control signal for the compensation actuator system for adjusting the position of the X-ray scattered radiation absorption grid depending on the received motion state data and depending on the determined quality measure. Determining the control signal includes optimizing the quality measure. The method further includes a step of outputting the control signal determined to the compensation actuator system in order to compensate the shadow of the X-ray scattered radiation absorption grid.

The technique may also be referred to as smart grid X-ray imaging with an intelligent control method.

The steps of the method may be executed repeatedly and/or iteratively (for example at runtime and/or in real time), for example when implemented by iterative learning control (ILC), for example as a function approximator. This provides the provision of a control loop that gradually increases the quality of the X-ray image by adapting the control signal to the optimized quality measure.

ILC is a method for tracking the control of systems that operate in an iterative or repetitive mode, such as, for example, the system for aligning and/or positioning the X-ray grid. For each aligning and/or positioning task, the system must execute the same action over and over again with high precision. This action is represented by the aim of accurately tracking a selected reference signal (for example, the quality measure) in a finite time interval. Repetition allows the system to improve tracking accuracy from repetition to repetition by learning the inputs required for accurate tracking of the reference. The learning process uses information from previous repetitions to improve the control signal so that eventually a suitable control action may be found by iteration.

Perfect tracking may in principle be achieved by an internal model (for example, as a standard or essential result of control engineering from the 1970*s*). For example, it is well known that the controller must contain an I component (integrating component) if constant disturbance variables are to be corrected (and for example if the system itself is not already self-integrating). This may, for example, be attributed, inter alia, to the fact that an integrator in the Laplace domain represents a model of a step signal.

When applied to the technique, the result of ILC is not "perfect" (and/or no perfect model of the system to be used is found). According to a first variant, it is possible to work with an approximatively selected model that is approximately suitable. The method (for example including ILC) will then still provide an improvement. The approximatively selected model may be required (for example only) for the design of the filters used in the ILC method.

Alternatively, or additionally, an internal model principle may lead to conditions under which perfect tracking (for example, ideally and/or according to the model assumption) may be achieved. The design of the control algorithm may still allow for many decisions that are required for the respective application.

A (for example, precisely defining) property (for example the quality measure) of the method may improve from execution to execution (for example, in the case of ILC) or (for example even) during execution (for example, when using a KAF).

A single execution of ILC may include a (for example, linear and/or sequential) sequence of the steps of the method for controlling the compensation actuator system. Alternatively, or additionally, the technical term "linear" vs. "non-linear" may be independent of the property of whether or not there is feedback (and/or repetition of method steps). For example, a linear system may include feedback (and/or repetition of method steps).

For example, the (for example, ultimately achieved) quality measure depends on the control signal (for example, determined and output). The control signal determined (and/or output) for example depends on the optimization of the quality measure.

The relationship (for example between the quality measure and the control signal) may be described as a "feedback" property and when the method is used accordingly, for example multiple times, the X-ray recording is thus controlled, for example the compensation actuator system is controlled.

The "feedback" property may (for example, depending on the choice of function approximator) be essential for successful compensation of the shadow of the X-ray scattered radiation absorption grid (X-ray grid for short), which is ultimately decisive for the image quality.

The "feedback" property may be used between individual motion state curves that are repeatedly approached (also: motion sequences and/or trajectories) (for example, when using ILC), in order to improve target variable patterns. Alternatively, or additionally, the "feedback" property may cause feedback during (also: within) the traversal of a motion state curve and/or change the pattern of the motion state curve (for example, if a kernel adaptive filter, KAF, is used in the method, for example as a function approximator).

A KAF is a kernel adaptive filter and thus a type of non-linear adaptive filter. An adaptive filter is a filter that adapts its transfer function to changes in signal properties over time by minimizing an error or loss function that characterizes how far the filter deviates from the ideal policy. The adaptation process is based on learning from a sequence of signal samples and is thus an online algorithm. A non-linear adaptive filter is a filter is which the transfer function is non-linear. Kernel adaptive filters implement a non-linear transfer function using kernel methods. In these methods, the signal is mapped to a high-dimensional linear feature space and a non-linear function is approximated as a sum over kernels whose domain is the feature space. If this is done in a reproducing kernel Hilbert space, a kernel method may be a universal approximator for a non-linear function. Kernel methods have the advantage that they have convex loss functions, have no local minima and are only moderately complex to implement.

The technique provides improved quality of the recorded X-ray image, for example in real time (and/or during operation of the X-ray device, in short: at runtime) to be achieved.

The technique provides relative shifts between the positions of the X-ray source and detector (and/or the X-ray grid attached to the detector) of the X-ray device to be compensated with the aid of the compensation actuator system (actuator system for short). As a result, shadowing (also: shadows) of the primary X-ray beam due to a shifted position of the X-ray grid (also: raster) in the recorded X-ray image (also: radiograph and/or X-ray recording) may be compensated. Alternatively, or additionally, the technique provides the quality, for example sharpness and/or detail accuracy, of an X-ray recording to be improved.

The X-ray grid may be configured as a predominantly two-dimensional element made of an X-ray absorbing material. The base area of the X-ray grid may for example be adapted to the surface of the detector and/or match it. At least one compensation actuator system may be configured to adjust the X-ray grid, for example to adjust it relative to the surface of the detector. The compensation actuator system may include at least two actuators for translational shifting and/or tilting of the grid in the two main axes in the plane of the grid.

Effects due to manufacturing and assembly tolerances, which are conventionally not taken into account (or cannot be taken into account) in simulation models based on rigid-body models and/or (for example, elastic) multi-body dynamic models, may be compensated by the control of the compensation actuator system, thus improving the quality of a recorded X-ray image.

As mentioned above, the compensation actuator system may include one or more compensation actuators. For example, the compensation actuator system may include two compensation actuators. Each compensation actuator may adjust the X-ray grid along a direction (for example, along a detector plane and/or along a base area of the X-ray grid). Adjusting the X-ray grid may include adjusting the detector (for example, shifting and/or tilting the detector plane). Alternatively, or additionally, the X-ray grid may be (for example permanently) attached to the detector and/or be mounted on the detector (for example as not adjustable relative to the detector.

Compensation (for example along a direction) may include tilting and/or shifting the X-ray grid and/or the detector (for example along the direction). Alternatively, or additionally, compensation may include tilting and/or shifting the X-ray source.

The pivotable arm may also be referred to as a gantry (and/or framework). Alternatively, or additionally, the pivotable arm may include a C-arm.

Compensating the shadow by changing a relative position of the X-ray grid (and/or detector) and the X-ray source may also be referred to as active tracking, fine-tuning or adjustment (for example, of the X-ray grid, the detector and/or the X-ray source).

Compensating the shadow provides higher aspect ratios (and/or a greater height of slats, for example with a non-vanishing angle of inclination, in relation to length and/or width of a raster projected onto the base area, and/or in relation to the distance between adjacent slats) than in conventional X-ray grids.

The relative (for example positional) shifts between the X-ray source and detector in the detector plane may also be referred to as deflections and/or migrations.

Improving the quality of the X-ray image may provide improved diagnosis and/or more targeted treatment of a patient. Alternatively, or additionally, a reduction in the radiation dose required to achieve a specified image quality may be provided.

For example, during an X-ray recording, for example angiography, the use of an X-ray grid may achieve greater selectivity of the primary X-ray beam from scattered radiation resulting in a reduction in the radiation exposure of patients and medical staff while improving image quality.

"In real time" may also be referred to as "at runtime", for example of the X-ray recording (and/or the X-ray fluoroscopy procedure).

"In real time" may mean that the method is executed so quickly that the passage of real time does not need to be slowed down in order to apply the method (for example, to record an X-ray image). Alternatively, or additionally, in real time (and/or at runtime) may mean that the technique may be applied to compensate the shadow of the X-ray grid during the recording of the X-ray image (and/or without, for example significant, delays) and for example during image reconstruction.

For example, when determining the control signal using actual motion state data (for example by a KAF), a real time capability is advantageous (and/or necessary, possibly even mandatory).

Alternatively, or additionally, when determining the control signal (for example only) on the basis of target motion state data, the technique may be applied before recording the X-ray image. For example, the control signal may be determined using target motion state data before the recording of the X-ray image (for example, in a planning phase) (for example, by ILC) and/or may be less time critical.

Depending on the technical embodiment, such a real-time property between image evaluation for quality determination and driving the actuator system may be almost mandatory (for example, in a variant with a KAF) or not (for example, in a variant with ILC).

Alternatively, or additionally, (for example active) compensation, for example in real time, may provide the prompt provision of high-quality X-ray images, for example while the patient is still in the recording position. Alternatively, or additionally, improving the quality of the X-ray image, for example in real time, provides a quick assessment of whether further X-ray images are required. Furthermore, Alternatively, or additionally, compensating the shadow, for example in real time, provides future (for example, several days or weeks later) follow-up appointments (for example, for further recordings, to discuss the diagnosis and/or to discuss a treatment plan).

Pivoting may include translational and/or rotational movements.

The pivotable arm (and/or the pivotably mounted X-ray device) may include translational and/or rotational degrees of freedom. For example, the X-ray device may include a C-arm, for example with five independent degrees of freedom. Alternatively, or additionally, the X-ray device (and/or the pivotable arm), for example the C-arm, may also include more or fewer than five independent degrees of freedom.

The X-ray grid may also be referred to as a detector grid. The X-ray grid may include slats (for example, made of metal, for example lead) that extend away from a base area.

The base area of the X-ray grid may correspond to a detector plane. Alternatively, or additionally, the position of the X-ray grid along the detector plane may be parameterized by two-dimensional (2D) coordinates, for example (x,y).

A reset position (also: referred to as a neutral position or unshifted position) of the X-ray grid may include that the X-ray source and detector of the X-ray device are arranged perpendicularly one above the other (or one below the other) and that a focal point (also: focus point) of an X-ray beam emitted by the X-ray source is mapped onto a predetermined point (for example the center point) of the X-ray grid.

The X-ray image may also be referred to as an X-ray recording and/or radiograph. Alternatively, or additionally, the X-ray image may include a temporal sequence of individual (and/or instantaneous) X-ray images.

The distance between the X-ray source and X-ray grid may be between 90 centimeters (90 cm) and two meters (2 m), for example 1.2 m.

The detector on which the X-ray grid is arranged may, for example, weigh 50 kg. Alternatively, or additionally, the pivotable arm may be elastically deformed by the movements captured in the motion state data and/or the motion state.

The width and/or diameter of the X-ray grid may be between ten centimeters (10 cm) and fifty centimeters (50 cm), for example between 20 cm and 45 cm. Alternatively, or additionally, a surface of the X-ray grid may be between 100 $cm^2$ and 2500 $cm^2$, for example between 20 cm×20 cm and 45 cm×45 cm.

The X-ray grid may include a rectangular, for example square, base area. Alternatively, or additionally, the X-ray grid may include a round, oval, or circular base area.

The height of the X-ray grid (and/or the height of the slats of the X-ray grid) may be between 5 mm and 2 cm. Alternatively, or additionally, the ratio of height to base area of the X-ray grid may be one to ten (1:10) or have a value of one to a number greater than ten.

In a conventional X-ray grid, the slats may extend perpendicularly in relation to the base area. Alternatively, or additionally, in an X-ray grid (also referred to as a "smart grid" and/or focused raster), the central slats may extend (at least approximately) perpendicularly with angles to the perpendicular to the base area increasing toward the edge of the X-ray grid. Alternatively, or additionally, the slats may be aligned to a common focus point. The common focus point may correspond to the position of a punctiform X-ray source (for example without relative shifts of the X-ray source and detector caused by position adjustments).

The outer slats of the (for example, focused) X-ray grid may deviate from the perpendicular to the base area of the X-ray grid by up to a maximum angle of 20° (and/or $\pi/9$).

The X-ray grid may be produced by additive manufacturing. Alternatively, or additionally, the X-ray grid may include an X-ray absorbing material, for example a metal (for example as a manufacturing material), for example lead.

The slats of the X-ray grid may form a (for example, rectangular) raster and/or a (for example, hexagonal) honeycomb structure. The raster and/or the honeycomb structure may be filled with an X-ray permeable material, for example aluminum. The stability of the X-ray grid may be improved by filling the raster and/or the honeycombs.

The received motion state data (motion data for short) may include sensor data and/or control data of the X-ray device. The motion state data received as sensor data (for example including measurement data) may also be referred to as actual motion state data. Alternatively, or additionally, the actual motion state data may be assigned to a current and/or actual motion state. Furthermore, Alternatively, or additionally, the target motion state data may be assigned to a planned motion state. Alternatively, or additionally, the target motion state data may be received as control data for the X-ray device.

The motion state data may represent a motion state of the X-ray device and/or the components thereof (C-arm). Alternatively, or additionally, the motion state data may include the position and/or orientation of the pivotable arm. Furthermore, Alternatively, or additionally, the motion state data may include the speed and/or acceleration of a change in position and/or change in orientation of the pivotable arm.

When using ILC, target motion state data may for example be received (for example, directly). The target motion state data (also: target variable curves) may be changed in each repetition of the method steps (and/or in each iteration). Alternatively, or additionally, the actual motion state data (and/or actual motion states) may be indirectly incorporated into the achieved quality measure (and/or not explicitly used and/or determined in the method).

When using a KAF, both actual motion state data (and/or actual variables) and target motion state data (and/or target variables) may be used, for example for determining the control signal and/or the quality measure.

The shadow of the X-ray grid may be determined by a shifted position (also: relative shift) of the detector relative to the X-ray source of the X-ray device in dependence on the received motion state data.

The position of the X-ray grid arranged on the detector determined on the basis of the received motion state data may include a relative shift of the predetermined point (for example the center point) of the X-ray grid relative to the focal point of the X-ray beam emitted by the X-ray source.

The motion state may also be referred to as the system state or device state (for example of the X-ray device).

The relative shift may be caused by static forces, and/or dynamic forces. For example, the pivotable arm of the X-ray device may include an elastically deformable connection (for example a C-arm) between the X-ray source and the detector. Alternatively, or additionally, the pivotable arm (and/or the X-ray device) may include an elastically deformable support (for example dependent on the motion state) for the detector, including the X-ray grid.

When the X-ray device moves, for example the pivotable arm (for example the C-arm), the forces acting on it (for example, inertial forces of the different masses being moved, Coriolis forces) may cause deformation to occur, which is represented in the motion state data. For example, the pivotable arm (and/or the connection) may deform elastically when deviating from the rest position, for example due to gravity (also: gravitational force; gravitation). Alternatively, or additionally, inertia, centrifugal force and/or Coriolis force may cause deformation of the pivotable arm (and/or the elastically deformable connection) of the X-ray source and detector.

Gravitation may include a statically acting, position-dependent force on the pivotable arm and/or the X-ray device, for example the detector and X-ray source thereof. Alternatively, or additionally, dynamic forces (for example, inertial force, centrifugal force, and/or Coriolis force) may act on the pivotable arm and/or the X-ray device, for example the detector and X-ray source thereof in a position-dependent way (for example depending on a speed and/or acceleration of a change in position and/or change in orientation).

The quality measure may also be referred to as an error signal and/or quality signal. The quality measure reflects the quality of the X-ray image, for example with regard to minimizing the shadow. For example, a quality measure value of zero may correspond to an optimal (also: ideal) quality measure and/or an optimal quality of the X-ray image. Furthermore, Alternatively, or additionally, an optimal (for example, minimal) value of the quality measure may correspond to a minimal shadow of the X-ray grid on the X-ray image.

Optimizing the quality measure may include minimizing the shadow (for example on a recorded X-ray image).

Determining the control signal (and/or optimizing the quality measure) may include accessing a database. The database may include a table and/or a lexicon (also: dictionary). The table and/or the lexicon may include a plurality of datasets (also: —for example vectorial—data points). For each dataset, motion state data of the X-ray device may be assigned to a control signal of the compensation actuator system and a quality measure. For example, the quality measure determined may be assigned to a zero value of the control signal (and/or to non-activation of the compensation actuator system).

The table and/or the lexicon may have been created using measurement data. Alternatively, or additionally, the table and/or the lexicon may be expanded during operation of the X-ray device. For example, after each recording of a (for example, final) X-ray image, a dataset (for example including motion state data of the X-ray device, a—for example optimized—quality measure and optionally a control signal, for example if the optimization of the quality measure was not a trivial matter) may be added to the table and/or the lexicon.

Determining and outputting the control signal using the motion state data of the X-ray device may also be referred to as data-driven learning control (for example of the compensation actuator system).

The (for example active) compensation of the shadow of the X-ray grid provides any image artifacts caused to be compensated and/or the quality of the X-ray image recorded (for example in real time) to be improved.

The, or each, X-ray image (and/or each radiograph) may be recorded as digital image data.

In one embodiment, the step of determining the quality measure may be executed for a test X-ray image. For example, a test X-ray image (and/or a Fourier-transformed test X-ray image) may be evaluated with respect to its quality measure. After compensating the shadow (for example, visible in the test X-ray image), a (for example, final) X-ray image may be recorded.

In a further embodiment, the quality measure is determined using the received motion state data, for example using the table and/or the lexicon.

In a further embodiment, the step of determining the quality measure (for example for a test X-ray image) may include capturing an image by a surround-view camera.

Determining the quality measure using the test X-ray image and/or using the image recorded with the surround-view camera may also be referred to as generating a ground truth.

The control signal output may include a target value for a current and/or a voltage at the compensation actuator system. Alternatively, or additionally, the control signal output may include (for example, updated and/or improved) target motion state data.

The method may be executed as cloud-based.

Alternatively, or additionally, the method may be executed on a local processor, a central processing unit (CPU), a neuromorphic processor unit or neural processing unit (NPU for short) and/or a graphics processing unit (GPU).

The pivotable arm may include a C-arm or be configured as such.

The pivotable arm (and/or the elastically deformable connection) between the X-ray source and detector may also be referred to as a gantry and/or for example include a C-arm.

The X-ray device (for example, with the elastically deformable connection configured as a pivotable arm, for example as a C-arm) may include an M-dimensional space of the (for example independent) degrees of freedom, for example with M=5 for a C-arm. Alternatively, or additionally, the motion state, for example of the C-arm, may include joint angles of axes, speeds of axes and/or accelerations of axes.

According to one embodiment, discrete values of the degrees of freedom and/or the state of motion may be predetermined.

The position of the X-ray grid arranged (for example, permanently) on the detector may include a position in a detector plane and/or in a plane perpendicular to a focal direction of the X-ray source of the X-ray device.

The position of the X-ray grid (and/or the detector) may be determined relative to the center point (and/or focal point) of an X-ray beam emitted by the X-ray source.

The position of the X-ray device and/or the pivotable arm may include a position and/or orientation in space.

The motion state may include a position, for example an orientation in space, and optionally a speed of position adjustment (for example for each degree of freedom) of the pivotable arm and/or the X-ray device.

According to one embodiment, the motion state may be two-dimensional (2D), for example, for each degree of freedom, and/or include position and speed (for example, as a change in position for each unit of time) of the X-ray device (for example, of the C-arm) as coordinates.

According to a further embodiment, the motion state may include discrete position signals (and/or positions) sampled at equidistant points in time and/or a series of one-dimensional (1D) coordinates (for example, for each, for example independent, degree of freedom), corresponding to the position of the pivotable arm of the X-ray device (for example, the C-arm) at a predetermined point in time in a time series.

The set of all positions, and optionally speeds, may also be referred to as the state space of the X-ray device and/or the pivotable arm).

The time series may be used to execute a time series analysis and/or time series prediction, for example without an independent measurement of a (for example, generalized) speed or (for example, generalized) acceleration.

The position of the X-ray grid that depends on the motion state of the X-ray device may also be referred to as a shift in the detector plane (or shift of the detector plane).

Alternatively, or additionally, the motion state of the X-ray device may be parameterized by generalized coordinates (for example, including angles) and/or generalized speeds (for example, including angular speeds).

The received motion state data may include target motion state data and/or actual motion state data (for example, captured, for example measured, by sensors).

The target motion state data may include motion state data determined in advance and/or control signals for the X-ray device (for example determined beforehand and/or "offline").

The actual motion state data may include (for example, actual and/or real) motion state data determined using sensor data. For example, a position and/or a speed may be measured. Alternatively, or additionally, acceleration may be determined using a (for example, measured) motor current of an actuator system of the pivotable arm (for example the C-arm).

Compensating the shadow may include tilting and/or shifting the detector (for example with the X-ray grid attached thereto). Alternatively, or additionally, compensating the shadow may include tilting and/or shifting the X-ray grid. Furthermore, Alternatively, or additionally, compensating the shadow may include tilting and/or shifting the X-ray source.

The compensation actuator system may include two compensation actuators. A first compensation actuator may be configured to tilt and/or shift the detector and/or the X-ray grid along a first direction of a detector plane. A second compensation actuator may be configured to tilt and/or shift the detector and/or the X-ray grid along a second direction of a detector plane.

The first direction may be different from the second direction. For example, the first direction may be perpendicular (90°) to the second direction.

Tilting along a direction may include rotation about an axis. The axis of rotation (axis for short) may extend along the (for example, x- or y-) direction. Tilting provides a detector plane to be changed.

In one embodiment, a relative shift of the X-ray source and detector, for example in each direction, of 5 mm to 10 mm may be compensated (for example actively) by the compensation actuator system. Alternatively, or additionally, in one embodiment, tilting may include rotation of up to 10° (and/or up to $\pi/18$), for example between 5° and 10° (and/or between $\pi/36$ and $\pi/18$), for example for each direction.

A suitable numerical range in which the compensation actuator system acts may depend on the geometry of the pivotable arm (for example the C-arm) and/or the X-ray device.

Alternatively, or additionally, shifting along a direction may include parallel shifting in the detector plane.

The method may further include a step of outputting the recorded X-ray image including compensating, for example in real time, of the shadow of the X-ray grid.

Outputting the recorded X-ray image may include artificial intelligence-based (AI-based) image reconstruction (for example, by a neural network, NN). Alternatively, or additionally, the X-ray image output may include "calculating out" and/or subtracting the X-ray grid (and/or a pure image of the raster) from the recorded X-ray image (for example with a patient placed between the X-ray source and detector).

The quality measure may include a quality measure for each direction, for example along the detector plane. The quality measure may for example include two (for example independent) values for the first direction of the detector plane and for the second direction of the detector plane. Alternatively, or additionally, the quality measure for each direction of the detector plane may be used to determine a control signal for a compensation actuator (for example, the first and/or second compensation actuator).

Determining the quality measure may include a comparison with one or more datasets in a lexicon. One or each dataset in the lexicon may include a motion state, a quality measure and optionally a control signal to compensate the shadow of the X-ray grid. Alternatively, or additionally, one or each dataset in the lexicon may include a temporal sequence (also: time series) of motion states, quality measures and optional control signals. The temporal sequence may include a (for example, predetermined) number of time steps. The (for example, predetermined) number of time steps may also be referred to as time embedding). Alternatively, or additionally, a history of the relevant data, for example the state of motion and associated quality measure, and optionally the control signal, for example for each time step, may be stored in the lexicon.

Alternatively, or additionally, the lexicon may include control signals defined as "zero" for which the compensation actuator (for example, the corresponding compensation actuator for each direction of the detector plane) is not controlled (for example not actively controlled).

Determining the quality measure may include evaluating contrasts in an X-ray image, for example in a Fourier-transformed X-ray image.

The, for example Fourier-transformed, X-ray image may include a predetermined (for example periodic) pattern of amplitude maxima (and/or maximum brightnesses; also: peaks) and amplitude minima (and/or minimum brightnesses) of one or more low-frequency fundamental waves of the X-ray beam. Deviations from the predetermined (for example periodic) pattern (also: periodicity) and/or attenuations of contrasts of amplitude minima and amplitude maxima in the Fourier-transformed X-ray image (and/or increasing homogeneity of the, for example, Fourier-transformed image) may be indicative of a deterioration of the quality measure of the X-ray image. Alternatively, or additionally, a sum of amplitudes of local maxima may be correlated with (for example, inversely proportional to) the quality measure. Furthermore, Alternatively, or additionally, a reduction in a number of characteristic frequencies may be indicative of a deterioration of the quality measure.

The Fourier transform may include a fast Fourier transform (FFT).

The quality measure may be measured by a shift vector with the aid of phantom images (and/or calibration images).

A phantom image and/or a calibration image may be an X-ray image recorded of a phantom or object with known image properties using the X-ray grid, for example without a patient between the X-ray source and detector.

Alternatively, or additionally, the quality measure may be determined (and/or calculated) from the image data according to an evaluation to be established (for example, during development), for example as a formula and/or an algorithm. During development, phantom images (and/or phantoms) may be used to develop (and/or design) the determination rule (and/or calculation rule, for example the formula and/or the algorithm). Alternatively, or additionally, the ground truth and/or the kind of image to be expected according to the phantom used may be unknown during the development phase.

Alternatively, or additionally, phantom images (and/or phantoms) may be good enough for the result also to be suitable for clinical use. Alternatively, or additionally, an extension of the technique, (for example, at least theoretically) includes the fact that the method may also be applied at runtime of the device for improvement or tracking.

The shift vector may include and/or parameterize a deviation (for example an actual deviation) of the focal point on the X-ray grid compared to calibration data without migration. The partial shadowing caused by the shift due to "wrong" angles in comparison to the design of the slats of the smart grid may be at least partially compensated by a tilt position.

The quality measure may be used as a basis for controlling the compensation actuator system. Alternatively, or additionally, the quality measure may be learned (for example, using the motion state data). Furthermore, Alternatively, or additionally, the quality measure may be adapted (for example optimized), for example in the step of determining the control signal.

At least the steps of determining the quality measure of the X-ray image and determining the control signal for the compensation actuator system may be executed repeatedly and/or iteratively. For example, the repetitions and/or iterations are executed until the quality measure determined is within a predetermined value range (and/or a predetermined minimum quality of the X-ray image is achieved after compensation).

Alternatively, or additionally, the step of receiving motion state data, of outputting the control signal determined, and/or (for example in the case of end-to-end learning) of outputting the recorded X-ray image may be executed repeatedly and/or iteratively.

Determining a control signal for the compensation actuator system may include machine learning (ML) and/or reinforcement learning (RL).

Reinforcement learning (RL) may include a software agent and one or more reward signals. The reward signals may correspond to optimization of the quality measure.

A policy, for example in RL, may include a collection of probability measures. The policy may be learned iteratively (also: step-by-step). For example, optimization of a quality measure may be learned iteratively using motion state data and control signals. Alternatively, or additionally, a control signal may be learned iteratively based on the motion state data and a (for example) predetermined quality measure.

RL may include one or more parameters of a control law as an action space. Alternatively, or additionally, a state space (for example, for ML and/or RL) may be continuous. Furthermore, Alternatively, or additionally, the action space may be continuous.

Policy learning may also be referred to as "policy search" and/or include an actor-critic algorithm. Alternatively, or additionally, policy learning may include proximal policy optimization (PPO) (for example, optimization of the quality measure).

The actor-critic algorithm may be an asynchronous advantage actor-critic (A3C) algorithm.

Alternatively, or additionally, ML and/or RL may include concurrent learning, for example to provide adaption to unknown influencing variables (which may also be referred to as disturbance variables) on the shadow of the X-ray grid.

The disturbance variable may, for example, include tilted and/or skewed attachment of the detector to the pivotable arm (for example the C-arm).

Alternatively, or additionally, the disturbance variable may include wear and/or an ageing process of the X-ray device.

Alternatively, or additionally, ML and/or the RL may include fuzzy logic).

ML and/or RL may be used to learn an adaptation of target variables (for example a shift to a calibration image) by the control signals. Alternatively, or additionally, one or more target variables may include the quality measure (for example for each direction of the detector plane).

Determining the control signals (for example by ML and/or RL) may be adaptive and/or repetitive.

Determining the control signal may include iterative learning control (ILC).

ILC is for example suitable in cases where disturbance variables are periodic and/or repeatable.

In ILC, a control signal at a (for example discrete) point in time may be described by a control signal and an error signal (also: quality signal and/or quality measure) at the previous (for example discrete) point in time by a first filter (for example, designated Q), which acts on the control signal and the error signal, and a second filter (for example, designated with L), which acts on the error signal. For example, the filters Q and L may have a multiplicative effect on the error signal.

ILC provides acausal filtering, for example because filters and/or control signals are changed from one iteration step to the next.

ILC may include controlling a target variable (for example, the control signals for the compensation actuator system for achieving the optimal quality measure). Alternatively, or additionally, an actuator of the compensation actuator system may include a motor controller). The target variable may include a current and/or voltage of the electric drive controller of the actuator.

ILC is for example suitable for repeatable (and/or non-linear) disturbance variables.

Alternatively, or additionally, a basic concept model and/or a first principle model may be used to linearize device dynamics and/or system dynamics (for example, of the X-ray device) at (for example suitably selected) points and/or a $H_\infty$ design may be used.

$H_\infty$ methods may be used in control engineering to synthesize robustly stabilizing controllers that achieve robust performance with respect to weighted transfer functions by mathematic optimization.

The first principle model may be created based on a fundamental physical understanding (and/or based on fundamental physical principles) (for example, with respect to conservation of energy and/or mass inertia).

The control signal may be determined based on calculations (for example, of the quality measure and/or for example high-frequency error signals) from image data.

In each embodiment of the technique, a time-continuous signal pattern may be discretized (for example as sampling at equal intervals, for example with sampling steps k).

Determining the control signal may include kernel adaptive identification feedforward extrapolation.

Kernel adaptive identification feedforward extrapolation may include learning a relationship between the control signal and quality measure (and/or error signal) by a kernel adaptive filter (KAF), for example by time embedding.

Kernel adaptive identification feedforward extrapolation may be particularly suitable when the formation of the shadow of the X-ray grid is dominated by strongly non-linear effects. Alternatively, or additionally, kernel adaptive identification feedforward extrapolation is online-capable and/or may be applied in real time during recording of an X-ray image. Furthermore, Alternatively, or additionally, kernel adaptive identification feedforward extrapolation does not require repetitive and/or periodic signal patterns.

For example, due to the "kernel trick" common for KAFs, in which a determination of a similarity of defined points in a feature space based on inner products in the feature space by evaluating a positive definite kernel is used, kernel adaptive identification feedforward extrapolation provides more efficient and/or improved performance compared to conventional compensation techniques for the shadow of the X-ray grid.

The application of the "kernel trick" to the solution of control signal generation for suppressing image artifacts is not conventionally known.

KAF training data may include datasets in which the control signal is zero.

Kernel adaptive identification feedforward extrapolation may include an interpolation method in which a first calibration image is shifted step-by-step (and/or iteratively) and a deviation between the current X-ray image and the calibration image is determined. The quality measure includes the amount of shift with respect to a minimum deviation.

MR, RL, ILC and/or kernel adaptive identification feedforward extrapolation may provide generalization to previously unseen data (and/or data not used for training).

Previously unseen data may include the fact that not all possible movements are (and/or cannot be) performed to generate the training data set. Alternatively, or additionally, a predetermined (and/or finite) amount of data (and/or datasets) may be used, for example, one hundred (100) different (and/or discrete) positions may be approached. The previously unseen data may include continuous positions (for example not equal to the approached positions), up to the quantization solution in the place after the decimal point, any number of positions.

Previously unseen data and (for example nonetheless) a good generalization capability may achieve a good result of the technique for compensating the X-ray grid shadow, for example even if similar data have not yet been available for training.

Alternatively, or additionally, the previously unseen data may be assigned to wear or to other effects that occur over a (for example long) period of time (and which, for example, change the motion state data). For example, gear properties (for example, of the pivotable arm) may change due to changes in friction coefficients, which may, for example, be temperature-dependent. Alternatively, or additionally, the temperature in the gear may depend on how long the X-ray device has been in continuous use and/or whether a space in which the X-ray device is arranged is heavily air-conditioned. The expectation of a good algorithm (for example MR, RL, ILC and/or kernel adaptive identification feedforward extrapolation) may include the fact that, despite the use of previously unseen data (for example state-of-motion data), the respective algorithm provides usable return values (for example, for the quality measure and/or control signal).

A KAF may include a kernel-based learning method. Alternatively, or additionally, Gaussian process regression and/or support vector machine (SVM) may be used to determine the control signal.

A KAF may for example be suitable for solving non-linear regression problems. Alternatively, or additionally, a non-linear function may map an input to an output), by transforming the input into a high-dimensional feature space H.

For example, a Gaussian kernel, a kernel recursive least-squares (KRLS) method and/or kernel least-mean-squares (KLMS) method may be applied.

In each embodiment, a function may include a sum over weighted kernels. The weights (and/or coefficients of the individual kernels) may be calculated at runtime. Alternatively, or additionally, a lexicon may include training points (and/or weights), and optionally data points and/or changed weights added at runtime (for example, due to newly occurring target variable patterns).

In one embodiment, the cardinality (and/or number of datasets) of the lexicon may be restricted in order to provide the execution of the method with limited memory capacity, limited computing capacity and/or limited computing time.

A KAF may include a function that maps a (for example, current) motion state and a control signal to a quality measure. Alternatively, or additionally, the application of the KAF and/or kernel adaptive identification feedforward extrapolation may include a inversely learned function for predicting the control signal (for example based on the quality measure and motion state).

In each embodiment the motion state data, the quality measure and/or control signal may be sampled in a discrete-time manner and time embedding may be applied over a plurality of time steps in order to take account of dynamic effects. The motion state data, the quality measure and/or the control signal may in each case be assigned a prediction horizon, for example up to an order of the time embedding of the motion state data, the quality measure and/or the control signal.

An order of the time embeddings may be selected independently (and/or differently) for the motion state data, the control signal and the quality measure.

The independent (and/or different) choice of the orders of the time embeddings has the advantage that the dimension may be kept as small as necessary. For physical variables, the order may, for example, be two (2), for example since the underlying differential equations are of second order. For the dynamics of the quality measure, the order may, for example, be selected to be at least five (5), for example 25.

The KAF may be ignorant of whether a variable is physical or not. Alternatively, or additionally, a developer (and/or designer) may know which variables are physical (and/or which variables are non-physical) and this knowledge may be used to establish the order (for example, as small as possible, as large as required). In the case of movements, for example if physical variables from position to acceleration are relevant, second (2nd) derivatives may be relevant and/or order 2 may be defined (for example by the developer and/or designer).

In a further embodiment, the order of the time embeddings may be selected as identical for the motion state data, the control signal and/or the quality measure.

A predictive capability of the KAF may be determined by an error measure, for example a mean squared error (MSE) between predefined output data points and output data points estimated by the trained KAF for identical input data points. For example, the smaller the error measure, for example the MSE, the better the predictive capability may be.

Alternatively, or additionally, the KAF may only be able to estimate and/or predict the appropriate output data as accurately as possible based on new input data.

A predictive capability may be assigned to one or more steps into the future. For example, a predictive capability may decrease with the number of steps to be predicted (for example starting from a fixed point in time and/or time step).

The prediction horizon may be and/or include the next possible sampling step. Alternatively, or additionally, the prediction horizon may include an integer greater than one, for example ten (10), for example if no determination of a control signal is provided (and/or possible) in each sampling step).

Kernel adaptive identification feedforward extrapolation may take place iteratively (and/or step-by-step), for example in real time and/or during an X-ray recording process.

The choice of KAF algorithm may be changed during the lifetime of the X-ray device. For example, the kernel recursive least-squares (KRLS) method may be applied initially. Alternatively, or additionally, a forgetting mechanism may be introduced if the X-ray device deteriorates due to wear effects and/or ageing effects.

Setting hyperparameters of the KAF may influence the learning policy of the selected algorithm (for example, improve convergence and/or avoid over-fitting), for example if a periodicity and/or a size of expected deviations is known.

Kernel adaptive identification feedforward extrapolation may provide multi-scale control, for example tilting along $M \geq 2$ degrees of freedom by M parallel (and/or independent) KAFs, for example, separately along the (x,y) directions of the detector plane.

Conventional KAF-based inverse control methods are based on reference models, which, however, are not applicable to imaging methods (for example X-rays). Other conventional KAF-based methods do not use reference models at all. Alternatively, or additionally, the technique differs from conventional KAF-based methods in novel generalization capabilities in order to extrapolate new control signals.

Determining the control signal may include end-to-end learning.

According to one embodiment, the control of the compensation actuator system may learn rewards (for example directly) from one or more X-ray images.

End-to-end learning may include deep reinforcement learning and/or a deep convolutional neural network (deep CNN).

A label (and/or quality measure) of an X-ray image may be determined on the basis of a reference image and/or on the basis of an assessment, for example a quality assessment, by an expert (for example, a radiologist).

A control signal may be determined on the basis of a quality measure (and/or label) and without capturing motion state data. Alternatively, or additionally, end-to-end learning may improve the generalizability of the technique.

According to an apparatus aspect, a computing apparatus is provided for controlling a compensation actuator system for compensating a shadow of an X-ray scattered radiation absorption grid in an X-ray image recorded with a pivotably mounted X-ray device, for example in real time.

The computing apparatus includes a receiving interface configured to receive motion state data indicative of a motion state of an X-ray device. The X-ray device is mounted on a pivotable arm. The motion state is assigned to a time of recording of an X-ray image by the X-ray device.

The computing apparatus further includes a quality measure determining unit configured to determine a quality measure of the X-ray image with respect to a shadow of an X-ray scattered radiation absorption grid which is arranged on the detector of the X-ray device.

The computing apparatus further includes a control signal determining unit configured to determine a control signal for a compensation actuator system for adjusting the position of the X-ray scattered radiation absorption grid depending on the received motion state data and depending on the determined quality measure. Determining the control signal includes optimizing the quality measure.

The computing apparatus further includes a control signal output interface configured to output the determined control signal to the compensation actuator system in order to compensate the shadow of the X-ray scattered radiation absorption grid.

The computing apparatus may include an X-ray image output interface configured to output the recorded X-ray image including compensating, for example in real time, the shadow of the X-ray scattered radiation absorption grid.

The computing apparatus may be configured to execute one or more steps of the method according to the method aspect. Alternatively, or additionally, the computing apparatus may include one or more features disclosed in connection with the method according to the method aspect.

According to a system aspect, a system is provided for controlling a compensation actuator system for compensating a shadow of an X-ray scattered radiation absorption grid in an X-ray image recorded with a pivotably mounted X-ray device, for example in real time.

The system includes an X-ray device mounted on a pivotable arm with an X-ray scattered radiation absorption grid. The system further includes a computing apparatus according to the apparatus aspect. The system further includes a compensation actuator system. A receiving interface of the compensation actuator system is configured to receive the control signal determined from the control signal output interface of the computing apparatus.

The system may be configured to execute the method according to the method aspect.

According to a further aspect, a computer program product is provided. The computer program product includes program elements which cause a computing apparatus to execute the steps of the method for controlling a compensation actuator system for compensating a shadow of an X-ray scattered radiation absorption grid in an X-ray image recorded with a pivotably mounted X-ray device, for example in real time, according to the method aspect when the program elements are loaded into a memory of the computing apparatus.

According to yet a further aspect, a computer-readable medium is provided on which program elements are stored which may be read and executed by a computing apparatus in order to perform steps of the method for controlling a compensation actuator system for compensating a shadow of an X-ray scattered radiation absorption grid in an X-ray image recorded with a pivotably mounted X-ray device, for example in real time, according to the method aspect when the program elements are executed by the computing apparatus.

The above-described properties, features and advantages and the manner in which they are achieved will become clearer and more plainly comprehensible in the light of the following description and the embodiments which are explained in more detail in conjunction with the drawings. The following description does not restrict the embodiments to the embodiments contained therein. The same components or parts may be provided with the same reference signs in different figures. The figures are not generally shown true to scale.

BRIEF DESCRIPTION OF THE DRAWINGS

FIG. 1 depicts a flow chart of a method for controlling a compensation actuator system for compensating a shadow of an X-ray grid in an X-ray image recorded with a pivotably mounted X-ray device, for example in real time, according to an embodiment.

FIG. 13 depicts an iterative development of a control signal and of a quality measure when iterative learning control (ILC) is used according to an embodiment.

DETAILED DESCRIPTION

FIG. 1 schematically depicts an example of a flow chart of a (for example computer-implemented) method for controlling a compensation actuator system for compensating a shadow of an X-ray scattered radiation absorption grid (X-ray grid for short) in an X-ray image recorded with a pivotably mounted X-ray device, for example in real time. The method is generally designated with reference sign 100.

The method 100 includes a step S102 of receiving motion state data indicative of a motion state of the X-ray device. The X-ray device is mounted on a pivotable arm. The motion state is assigned to a time of recording of the X-ray image by the X-ray device.

The method 100 further includes a step S104 of determining a quality measure of the X-ray image with respect to a shadow of the X-ray grid, which is arranged on the detector of the X-ray device.

The method 100 further includes a step S106 of determining a control signal for a compensation actuator system for adjusting the position of the X-ray grid depending on the received S102 motion state data and depending on the determined S104 quality measure. Determining S106 the control signal includes optimizing the quality measure.

The method 100 further includes a step S108 of outputting the determined S106 control signal to the compensation actuator system in order to compensate the shadow of the X-ray grid.

The method 100 may include a step S110 of outputting the recorded X-ray image including compensating (for example, by the determining step S106), for example in real time, the shadow of the X-ray grid.

At least some of the method steps S102, S104, S106 and S108 (and for example S110) may be executed repeatedly, for example iteratively. This provides the control of the compensation actuator system to be gradually improved.

By way of example, FIG. 1 shows schematically that the steps S104 and S106 of determining the quality measure of the X-ray image or of the control signal for the compensation actuator system may be executed repeatedly. The (for example, expected) quality measure may be determined S104 again for a determined S106 control signal.

In a further embodiment shown in FIG. 1, after sample X-ray image has been output S110, new motion state data may be received S102 and the determination S104 and S106 of the quality measure of the X-ray image or the control signal for the compensation actuator system may be repeated.

Figure 2:
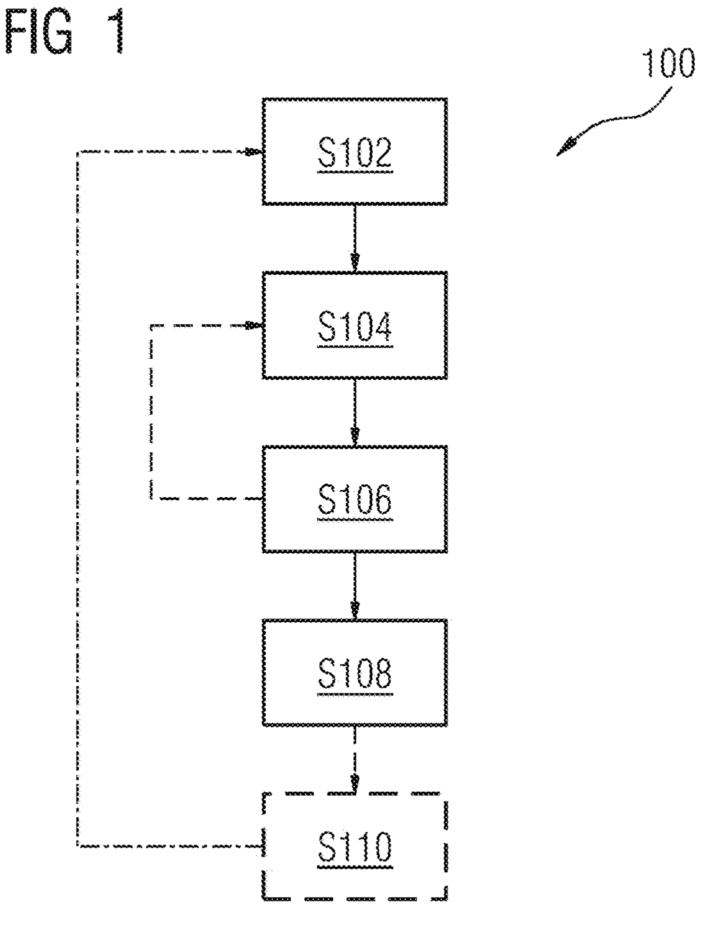
FIG. 2 depicts an overview of the structure and design of a computing apparatus for controlling a compensation actuator system for compensating a shadow of an X-ray grid in an X-ray image recorded with a pivotably mounted X-ray device, for example in real time, according to an embodiment.

FIG. 2 schematically shows an example of the architecture of a computing apparatus for controlling a compensation actuator system for compensating a shadow of an X-ray grid in an X-ray image recorded with a pivotably mounted X-ray device, for example in real time. The computing apparatus is generally designated with reference sign 200.

The computing apparatus 200 includes a receiving interface 202 configured to receive motion state data indicative of a motion state of the X-ray device. The X-ray device is mounted on a pivotable arm. The motion state is assigned to a time of recording of the X-ray image by the X-ray device.

The computing apparatus 200 further includes a quality measure determining unit 204 configured to determine a quality measure of the X-ray image with respect to a shadow of the X-ray grid, which is arranged on the detector of the X-ray device.

The computing apparatus 200 further includes a control signal determining unit 206 configured to determine a control signal for a compensation actuator system for adjusting the position of the X-ray grid depending on the received motion state data and depending on the determined quality measure. Determining the control signal includes optimizing the quality measure.

The computing apparatus 200 further includes a control signal output interface 208 configured to output the determined control signal to the compensation actuator system in order to compensate the shadow of the X-ray grid.

The computing apparatus 200 may include an X-ray image output interface 210 configured to output the recorded X-ray image including compensating (for example in real time) the shadow of the X-ray grid.

The receiving interface 202, the control signal output interface 208, and optionally the X-ray image output interface 210, may be arranged in an input output interface 212.

The quality measure determining unit 204 and the control signal determining unit may be configured by a processor 214 (for example including a CPU and/or a GPU).

The computing apparatus 200 may be configured to execute the method 100. For example, the receiving interface 202, the quality measure determining unit 204, the control signal determining unit 206, the control signal output interface 208 and optionally the X-ray image output interface 210 may be configured to execute steps S102, S104, S106, S108, and potentially S110.

A system (not shown) may include the computing apparatus 200 and an X-ray device mounted on a pivotable arm with an X-ray grid and a compensation actuator system. A receiving interface of the compensation actuator system may be configured to receive the control signal determined from the control signal output interface 208 of the computing apparatus 200.

Figure 3A:
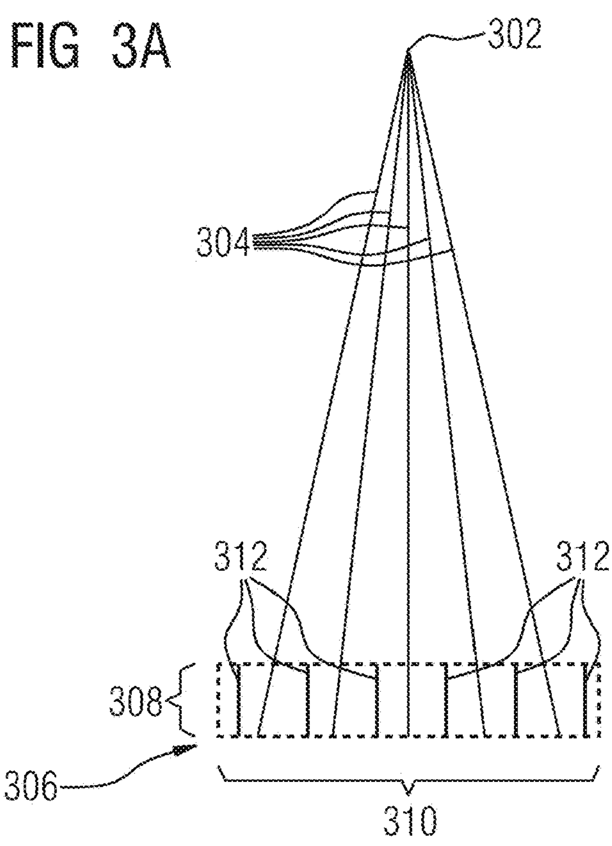
FIGS. 3A and 3B depict a conventional X-ray grid with slats perpendicular to a base area or a so-called "smart grid" with slats aligned in the direction of an X-ray source.

FIG. 3A shows a schematic example of a conventional X-ray grid with perpendicular (and/or mutually parallel) slats 312. The X-ray grid includes a height designated with reference sign 308 and a width, or a diameter, designated with reference sign 310, of a base area 306. Starting from the X-ray source 302, the X-ray beam fans out as shown schematically at reference sign 304.

In the case of the conventional X-ray grid shown in FIG. 3A, the shadow caused by the (for example, outer) slats is independent of the position of the X-ray grid in the detector plane parallel to the base area 306.

Figure 3B:
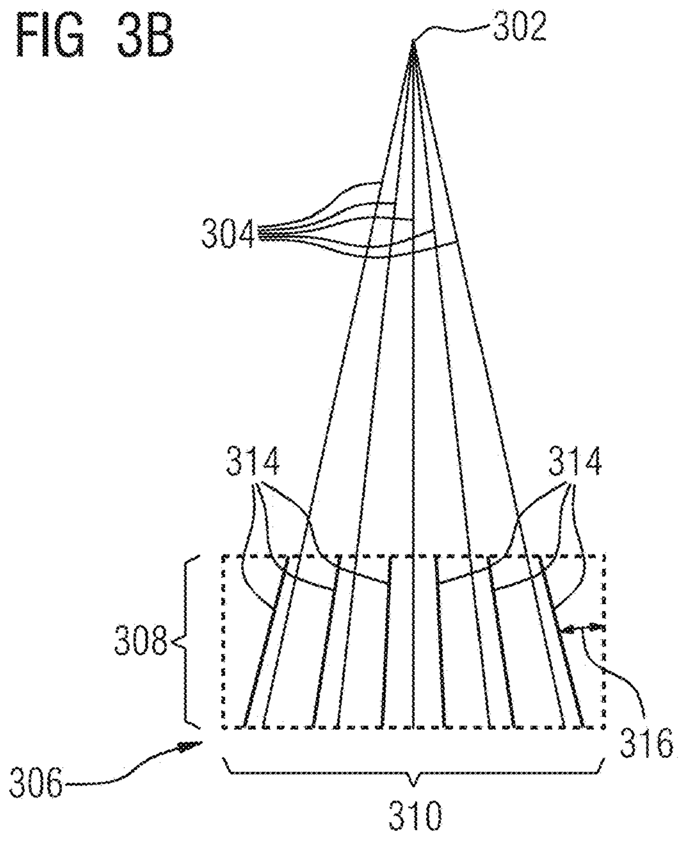

FIG. 3B shows an example of a "smart grid" (also: focused raster). The same variables as those shown in FIG. 3A are designated with identical reference signs. By way of example, a maximum angular deviation (for example, 20° and/or $\pi/9$) from a perpendicular of an outer slat 314 is shown at reference sign 316.

In the case of the "smart grid" in FIG. 3B, ideally (for example without any shift and/or migration of the detector), no shadowing occurs. A shift of the detector relative to the X-ray source 302 may result in differently pronounced shadows (for example dependent on the motion state of the X-ray device) of the slats 314 of the X-ray grid.

Figure 4:
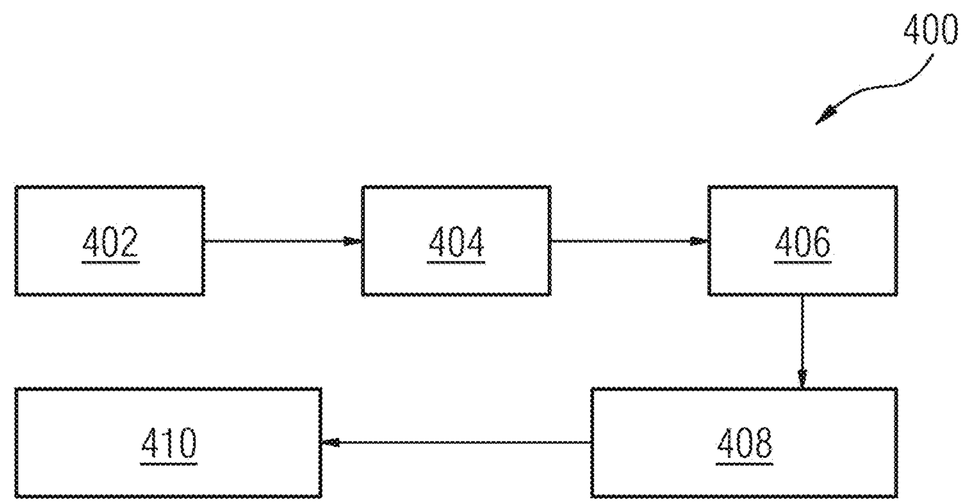
FIGS. 4 and 5 depict a technique known from the prior art for avoiding a shadow of an X-ray grid by an additional actuator system.

FIG. 4 shows an example of a conventional method 400 in which an elastostatic model of the dynamic effects is created and calculated at runtime in order to correct the relative shift between the emitter and the detector by correction drives and a Cardan suspension mechanism.

A trajectory (also: motion cycle and/or motion state curve) of a C-arm (as an example of a pivotable arm) is specified at reference sign 402. A real-time capable (for example, elastostatic) model of the mechanics of the C-arm is created and/or applied at reference sign 404. Deformation of the C-arm is determined (for example calculated) at reference sign 406. The relative shift between the emitter and the detector resulting from the deformation is determined at reference sign 408. A correction of the relative shift by two correction drives (and/or compensation actuators) is determined at reference sign 410.

Figure 5:
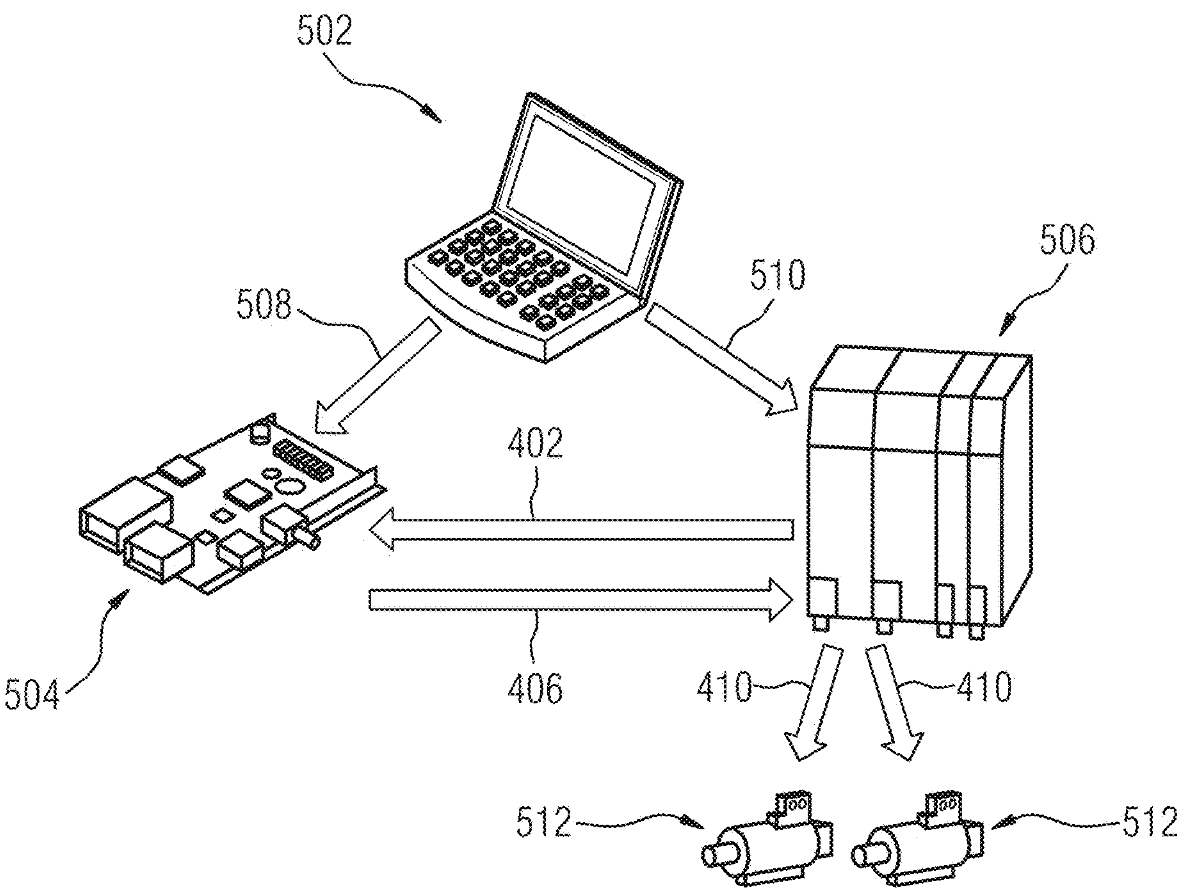

FIG. 5 shows components that may be used in the conventional method 400 shown in FIG. 4. A user interface of a computer (and/or a computing apparatus) is shown at reference sign 502. By way of example, a circuit board (and/or a mini-PC) of the computer (and/or the computing apparatus) or an external computing apparatus is shown at reference sign 504 on which the real-time capable (for example, elastostatic) model of the mechanics is executed or output thereto (and/or a code is generated) 508. In the conventional (for example, elastostatic) model of the mechanics, dynamic equations are generated from a simulation model and calculated on the mini-PC (and/or the circuit board) 504 at runtime and adjustments are made with a drive controller to one or more control units (for example, programmable logic controllers, PLCs) 506 of the correction drives (and/or correction actuators) 512, as shown schematically at reference signs 402 and 406.

As indicated at reference sign 510, the computer (and/or the computing apparatus) 502 projects the drive controller onto the control units (for example, PLCs) 506. The drive controller (for example, PLC) 506 may operate a subordinate control of one or more motors. A target variable for the drive controller (for example, PLC) 506 is usually calculated by another control unit (for example, in the schematically depicted computer 502).

FIGS. 4 and 5 show a simple prototype of an actively actuated mechanism for tracking the X-ray grid during operation. Herein, the X-ray grid, which is attached to the detector, is, for example, mounted so as to be tiltable in two axes, so that fine positioning is possible in order to kinematically compensate the shifts, which occur due to the elasticity of the C-arm, for example.

As shown schematically in FIGS. 4 and 5, the conventional solutions are based in principle either on static measurements at interpolation points and storage of values in a table (and/or position-related calibration) or on model-based calculation of the control commands for the correction drives.

The second variant of the model-based calculation of the control commands is based on the fact that an elastostatic model of the C-arm and the dynamic effects is created (for example manually and/or by engineering), which is real-time capable or may be calculated at runtime and is intended to calculate the relative shift between the emitter and the detector in order to compensate the shift by driving the correction drives accordingly.

In principle, the conventional method has the disadvantage that the achievable compensation accuracy for correcting the super grid depends on the modeling quality of the underlying model. However, the calculation of real-time capable models of the relevant deformation in each case that are at the same time highly precise is not a trivial matter and so it is necessary to work with approximations and model assumptions or model simplifications. Furthermore, there are effects on the real X-ray device, which are not taken into account by the model, or only taken into account with great difficulty, and thus may impair the informative value, for example if, due to manufacturing tolerances and/or assembly tolerances, the smart grid is attached to the detector in a slightly different way than that assumed in the model. Preliminary evaluations had already shown that such effects (for example the precision of the mechanical attachment of the X-ray grid on the detector) have a significant influence on the achievable quality of an X-ray image and may significantly impair the result.

For example, in contrast to conventional techniques, the technique is (for example, as far as possible) independent of the specific hardware system architecture.

Alternatively, or additionally to PLC-based control for the compensation actuator system, it is possible to use an embedded electronics board on which the real-time control of the pivotable arm (for example the C-arm) and/or the control of the correction actuator system of the smart grid may be executed (for example simultaneously and/or in parallel). Alternatively, or additionally, a GPU or GPU-like component may be used to provide fast calculation of an NN.

The technique (for example including the method 100 and/or the computing apparatus 200) provides active tracking of the X-ray grid (and/or raster) (for example, that may be necessary due to radiation physics). While it has conventionally been shown that active tracking of the X-ray grid is in principle possible (for example mechanically and/or in terms of control technology) and provides the use of a (high-aspect) super raster, the question of high-precision compensation of emitter shifting and/or detector shifting continues to be a lever for compensating the shadowing more precisely, enabling the use of super rasters with higher aspect ratios and thus improving the achievable image quality with a reduced radiation dose. Moreover, data-driven learning control also provides further advantages.

In the technique (for example including the method 100 and/or the computing apparatus 200), the control signals for the actuator system for compensation are calculated by a data-driven method, which, as a quality measure, is based directly on the image quality achieved as the ultimately relevant variable (and not, for example, on an assumed shift of the beam focus, which indirectly influences the image quality).

The following symbols and variables are used below:

$n \in \mathbb{N}$: number of movable degrees of freedom of the pivotable arm and/or gantry, for example, of a C-arm (where $n \geq M$, wherein M is the number of independent degrees of freedom);

$q \in \mathbb{R}^n$: (actual) joint angles of the axes and/or generalized coordinates;

$\dot{q} \in \mathbb{R}^n$: (actual) speeds (and/or time derivative) in generalized coordinates;

$\ddot{q} \in \mathbb{R}^n$: (actual) accelerations in generalized coordinates;

$q_d \in \mathbb{R}^n$: target joint angles of the axes and/or generalized coordinates;

$\dot{q}_d \in \mathbb{R}^n$: target speeds of the axes and/or generalized coordinates;

$y \in \mathbb{R}^m$: joint angles of the axes that actuate the tilting of the smart grid (where generally, m=2);

$y_d \in \mathbb{R}^m$: target joint angles of the axes that actuate the tilting of the smart grid;

$$\overline{x} = \begin{bmatrix} q \\ \dot{q} \end{bmatrix} \in \mathbb{R}^{2n}:$$

(for example dynamic and/or actual) motion state of the X-ray device (also: system);

$$\overline{x}_d = \begin{bmatrix} q_d \\ \dot{q}_d \end{bmatrix} \in \mathbb{R}^{2n}:$$

target variables of the state of motion;

$d \in \mathbb{R}^{n_d}$: (for example unknown) disturbance variables that may result in a deterioration of image quality;

$(x, y) \in \mathbb{R}^2$: coordinate directions in the detector plane;

$c_i \in \mathbb{R}_{\geq 0}$: overall quality measure of image quality, wherein $c_i=0$ in the case of perfect artifact compensation;

$c_x \in \mathbb{R}_{\geq 0}$: quality measure of the compensation in the x-direction, wherein $c_x=0$ in the case of perfect artifact compensation in this direction;

$c_y \in \mathbb{R}_{\geq 0}$: quality measure of the compensation in the y-direction, wherein $c_y=0$ in the case of perfect artifact compensation in this direction;

$q[k]=q(kt_s)$: discrete-time signal resulting from sampling with the sampling time $t_s$ from the continuous signal q(t)t; and $k \in \mathbb{N}_0$: discrete sampling time step.

One aim of embodiments of the technique is to determine (and/or calculate) the control signals for the compensation actuator system (and/or target variables) $y_d$ and to output them to the compensation actuator system (and/or control unit of the smart grid) at runtime in such a way that the quality measure is optimized (for example $c_i \rightarrow 0$), although (for example also unknown) disruptive influences d act on the system.

In further embodiments of the technique, the overall quality measure $c_i$ and/or the quality measures for each direction of the detector plane ($c_x$, $c_y$) may be determined (and/or calculated) from the medical X-ray imaging data.

Figures 6, 7, 8:
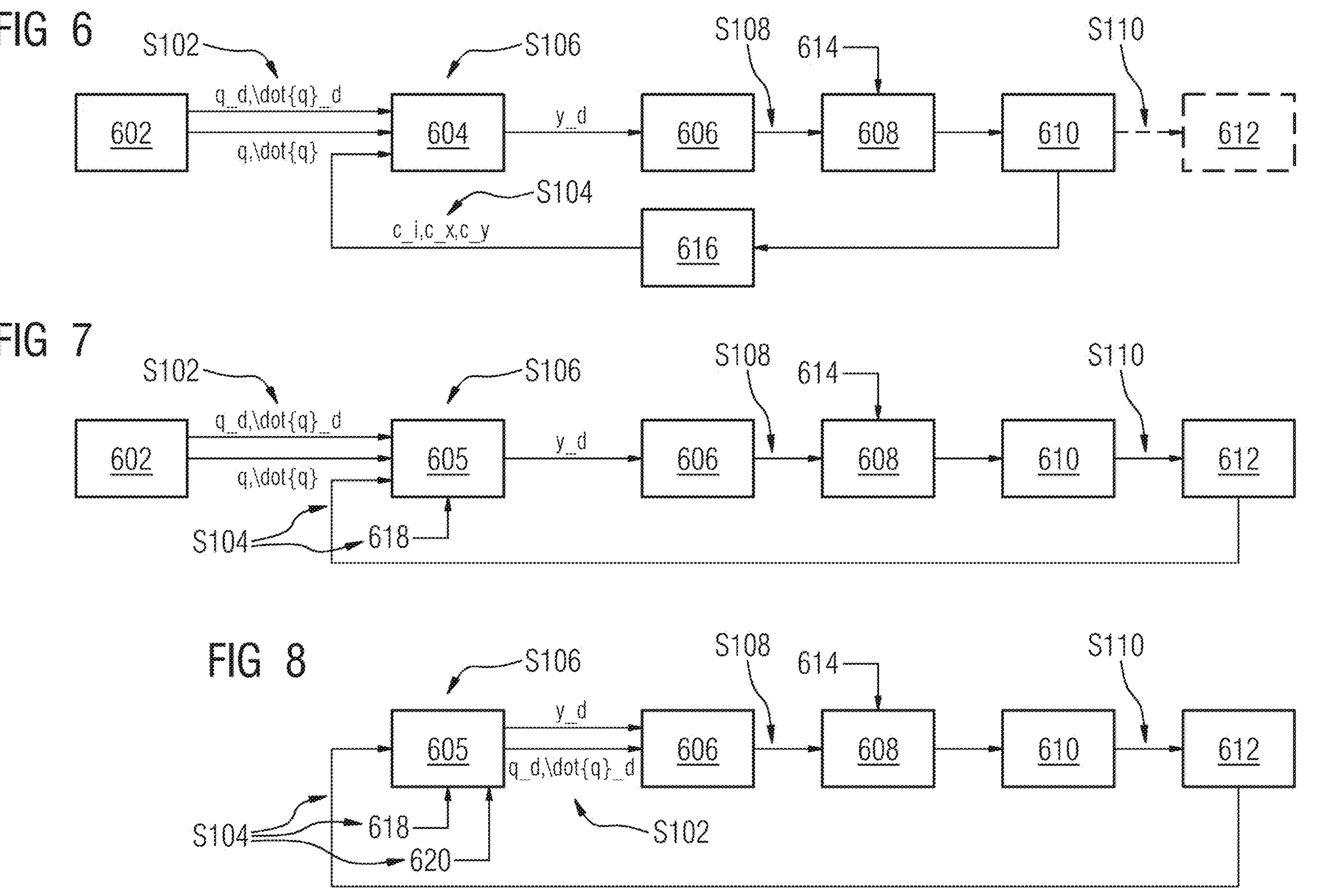
FIGS. 6, 7 and 8 depict schematic embodiments of the technique in which, for example, iterative learning control (ILC), kernel adaptive identification feedforward extrapolation, reinforcement learning (RL) or end-to-end learning may be used to realize a function approximator according to an embodiment.

FIG. 6 shows a first embodiment of the method 100.

This may be called an "intelligent method" since the control system and/or regulation system uses learning strategies and/or adaption strategies, for example from the field of artificial intelligence (AI) (for example, fuzzy logic, RL, NNs, and/or concurrent learning) in order to achieve an adaption to unknown influencing variables (see, for example, Schröder, Buss: Intelligente Verfahren: Identifikation und Regelung nichtlinear Systeme, Springer 2017 incorporated herein by reference).

In one embodiment, (for example, as shown in FIG. 6), the following assumptions are made:

The positions of the degrees of freedom of the pivotable arm (and/or the gantry, for example the C-arm) q and their time derivatives $\dot{q}$ are known at runtime. The positions q and speeds $\dot{q}$ are provided by the system control of the pivotable arm, likewise the target patterns $q_d$ and $\dot{q}_d$. The corresponding variables are combined to form the motion state $$\bar{x} = \begin{bmatrix} q \\ \dot{q} \end{bmatrix}.$$

First, the compensation actuator system of the smart grid is deactivated, i.e., $y_d=0$ (and/or there is no movement of the grid tracking). Depending on the motion state $\bar{x}$, a more or less good X-ray image is then obtained due to the known or unknown disruptive influences d. Disruptive influences could, for example, be the deflection of the pivotable arm (for example the C-arm), and/or dynamic forces, such as inertial forces or Coriolis forces, which result in the X-ray grid no longer matching the calibration and thus artifacts becoming visible in the X-ray image.

Based on the image processing, it is possible to calculate a quantitative quality measure describing the overall quality of the X-ray image obtained with respect to the identifiable artifacts due to the X-ray grid. The overall quality measure is referred to as $c_i$ below, where $c_i=0$ in the case of perfect artifact compensation. The quality measure may Alternatively, or additionally be described in an axis-dependent manner in the 2D-X-ray image by the variables $c_x$ and $c_y$. The axis-dependent description is, for example, relevant, if undesirable artifacts are only present in one dimension, for example, horizontally, but no (or only a few) artifacts are still visible vertically. The quality measures $c_i$, $c_x$ and $c_y$ are, for example, provided in method step S104 and optimized in step S106.

In order to ensure deterministic performance and certifiability of the approach, it may be necessary not to change the (feedback) controller (for example, the control of the pivotable arm, also: gantry control, and/or the control of the smart grid, also: smart grid control) by a learning component. It may (for example instead) be advantageous to leave the controller structure and controller parameters the same and only change the control signals.

In FIG. 6, the motion state (also: system position and/or system motion) $\bar{x}$ and/or $\bar{x}_d$ for receiving in step S102 of the method 100 is shown at reference sign 602. A calculation of a control target variable is shown at reference sign 604. This calculation may take place in step S106 of the method 100. The compensation actuator system of the smart grid is shown schematically at reference sign 606. X-ray imaging including the smart grid on the detector takes place at reference sign 608. The X-ray imaging is influenced by disruptive influences d, as shown schematically at reference sign 614. Image processing on the basis of which an X-ray image may be output as a useful medical image 612 takes place at reference sign 610. The determination (and/or calculation) of the quality measure, which may, for example, take place in step S106 as optimization of the quality measure and/or in step S104, in this embodiment as feedback for iterative optimization, is shown at reference sign 616.

Therefore, in the embodiment shown in FIG. 6, the target variables $y_d$ of the actuators, which may actively move the super raster, are generated at runtime in such a way that the quality measure is optimized (for example, c_i→0).

The embodiment shown in FIG. 6 may use different function approximators in order to optimize the quality measure and output one or more corresponding control signals.

A first embodiment of a function approximator includes iterative learning control (ILC). ILC methods (without applications for X-ray recordings) are known per se.

The basic assumption of ILC is that there is a repetitive task and/or a recurring disturbance. In the case of an X-ray device mounted on a pivotable arm, this corresponds to the assumption that the disturbance variables d that lead to artifacts are repeatable for a given $\bar{x}_d$, even though the pattern may be non-linear.

Figure 13:
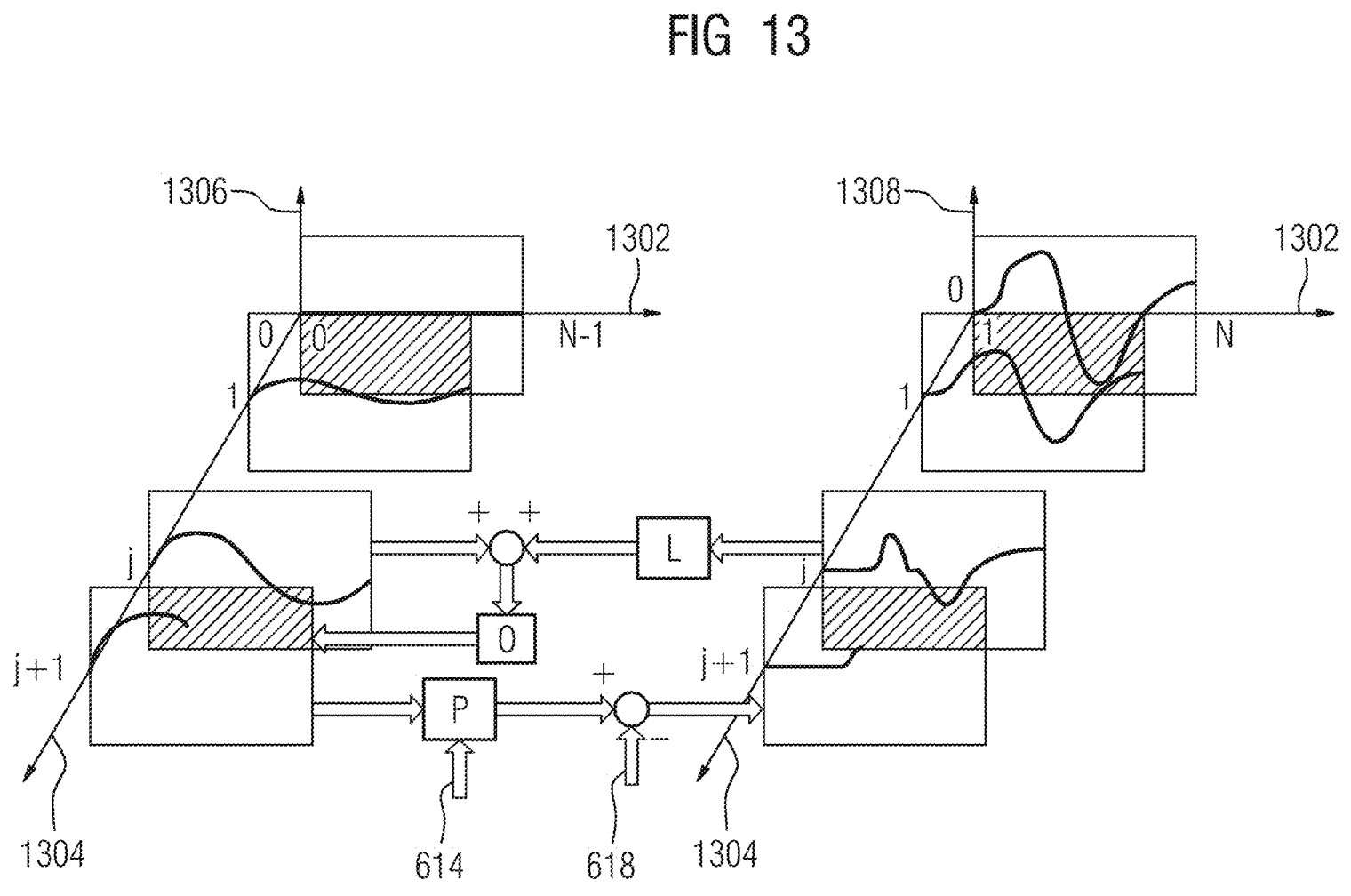

FIG. 13 shows an ILC schematic sketch. A sample time is shown at reference sign 1302, a count of iteration steps is shown at reference sign 1304 and a control signal $y_d$ is shown at reference sign 1306 (for example, a time-varying amplitude of the control signal, as shown schematically for each iteration). The quality measure $c_i$ is shown at reference sign 1308 (for example, a time-varying amplitude of the quality measure). A disturbance d is shown schematically at reference sign 1310 and a reference image is shown at reference sign 1312.

As shown schematically in FIG. 13 at higher iteration steps, an adaptation of the control signal $y_d$ is achieved from iteration to iteration by calculating the ILC, so that the quality measure $c_i$ is optimized (and/or decreases, for example, c_i→0). Here, an iteration refers to the repetitive task, i.e., a complete "sequence" of the control signal, for example, moving a C-arm by 180 degrees for orbital 3D imaging.

In computer-implemented signal processing, the time-continuous signal patterns of the physical variables are usually discretized. For example, the patterns of positions q(t) and/or speeds $\dot{q}(t)$ are sampled at times $t_0$, $t_1$, . . . . The discretized position signals $\{q[t]\}=\{q(t_0), q(t_1), \ldots\}$ and/or speed signals $\{\dot{q}[t]\}=\{\dot{q}(t_0), \dot{q}(t_1), \ldots\}$ are obtained as motion state data.

Since equally sampled variables are used in the time interval $t_s$, in the following they will also be written simply in short form as $q[k]=q(kt_s)$. Alternatively, or additionally, the control signals (and/or control variables) are for example calculated in a discrete-time manner by the computing apparatus 200 (and/or a computer) and then converted back into a physical-continuous variable (for example, current, voltage) by a motor controller.

The simplest ILC adaptation law is expressed as $$y_d^{i+1}[k] = Q\left(y_d^i[k] + Lc_1^i[k]\right). \quad (1)$$

Here, $$y_d^i[t]$$

designates the control signal variable pattern in the i-th iteration of the repetitive task. The initial control signal $$y_d^0[t]$$

may be calculated via a conventional control design. Alternatively, or additionally, may $$y_d^0 = 0$$

may be assumed. In the case $$y_d^0 = 0,$$

the complete control of the smart grid is learned using the ILC method.

The engineering task for applying the method consists in calculating the filters Q and L. A model-based design may be used for this purpose, wherein first-principle models and/or system models of the X-ray device are advantageously used. In this case, the dynamics (for example of the pivotable arm) of the X-ray device (also: system dynamics) may be linearized at suitable points and a robust filter design (and/or a robustness design the filters Q and L) may be used, for example, including a $\mathcal{H}_\infty$, design. The usual methods may be found in control engineering literature.

The use of conventional ILC methods in technical applications may be difficult if the requirement of a quality measure $c_i[k]$ available in each sampling time step k cannot be met, since the determination and/or calculation is carried out from the X-ray image data and is a computationally intensive operation that is not conventionally carried out in the (for example fast) cycle of the control system (for example, $t_s \approx 1\text{-}10$ ms). This technical difficulty may be circumvented by using more advanced ILC methods that may also operate with less high-frequency quality measures (and/or error signals). Such an advanced ILC method is, for example, described (and/or developed).

ILC may be seen as a (for example relatively simple) special form of an RL strategy for cases when a repetitive task is performed several times and the system disturbances of the system are also repetitive and predictable (for example, however, unknown). If the assumptions are not correct, more general RL methods may be used.

In a further embodiment, kernel adaptive identification feedforward extrapolation is used as a function approximator. Academic control literature includes very few or no publications on kernel adaptive identification feedforward extrapolation and it is best inferred from known references. For example, kernel (for example, kernel-based) adaptive filters (KAF) are not known for solving the problem of control signal generation in order to suppress image artifacts (for example in X-ray images).

In contrast to the ILC method, kernel adaptive identification feedforward extrapolation does not require repetitive and/or periodic signal patterns (for example for the quality signal, the control signal, and/or the motion state data). Overall, the performance of kernel adaptive identification feedforward extrapolation may be better than the performance of ILC since, on the one hand, the method learns efficiently due to the use of the "kernel trick" and, on the other, provides generalization of the relationships to previously unseen data (for example by machine learning, ML).

A modification of a kernel adaptive filter (KAF) is used for the technique (for example, a modification of a class of signal processing methods and are based on ML) in order advantageously to extrapolate the effects during operation (for example, elastic deformation of the pivotable arm of the X-ray device due to static and dynamic forces, temperature dependencies of gear behavior and/or wear) by the "kernel trick" and to introduce a counteraction into the control signal path.

KAF is known per se and is one of the kernel-based learning methods (which also include, for example, Gaussian process regression and/or support vector machine, SVP) to solve non-linear regression problems. This means that, for an input/output stream of data points $(x_i, y_i)$, the non-linear function $f_i(\bullet)$ underlying the relationship between input $x_i$ and output $y_i$ is estimated, $$y_i = f_i(x_i), \tag{2}$$

and this estimate is updated with each new data pair.

Figure 9:
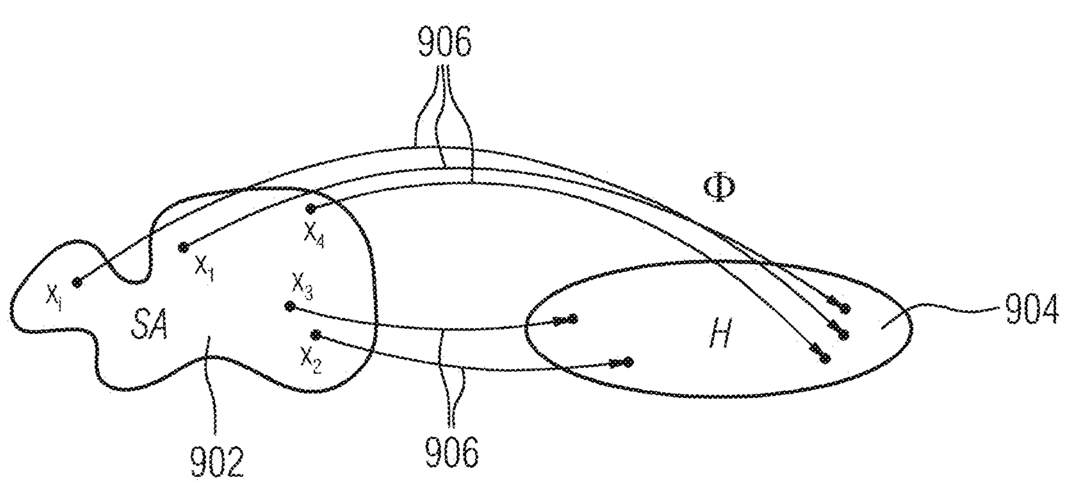
FIG. 9 depicts a schematic view of the "kernel trick" for determining data points according to an embodiment.

Kernel-trick-based extrapolation methods are based on a non-linear transformation of the data $x_i$ at reference sign 902 in FIG. 9 into a high-dimensional (for example implicit) feature space $\mathcal{H}$, as shown at reference sign 904 in FIG. 9. The calculation of the inner products in the feature space 904 required for ML may be determined by evaluating a positive definite kernel, $$\langle \Phi(x_i), \Phi(x_j) \rangle = \kappa(x_i, x_j), \tag{3}$$

wherein $\Phi$ is an example of non-linear mapping into the (infinite-dimensional) feature space at reference sign 906, which is generally not explicitly known. The only essential factor is that a similarity of data points in the feature space 904 may be determined. The feature space (and/or data in the feature space) 904 and the mapping 906 are not (for example, explicitly) calculated (and/or are not known, for example explicitly).

According to the "kernel trick", only the kernel function on the right-hand side of equation (3) needs to be evaluated (see Mercer's theorem). The "kernel trick" is for example suitable for non-linear relationships and unknown feature spaces, such as those that occur in the technique for compensating an X-ray grid shadow by adaptive and/or learning control of a compensation actuator system.

The kernel $\kappa$ may be referred as a metric of the high-dimensional feature space $\mathcal{H}$ (for example, at reference sign 904 in FIG. 9). Alternatively, or additionally, a distance between data points (for example, in the set SA at reference sign 902 in FIG. 9) in the feature space $\mathcal{H}$ may be large if the value of the kernel $\kappa$ is large.

There are many different kernel functions $\kappa$; the most commonly used kernel is the Gaussian kernel:

$$\kappa(x_i, x_j) = \exp\left(\frac{-\|x_i - x_j\|^2}{2\sigma^2}\right). \tag{4}$$

The Gaussian kernel in equation (4) provides many non-linear relationships (see equation (2)) to be represented with sufficient accuracy by a kernel development using training data, $$f_{KAF}(x) = \sum_{i=1}^{N} \alpha_i \kappa(x_i, x_j). \tag{5}$$

KAF algorithms, such as, for example, KRLS and/or KLMS, calculate the coefficients (and/or weights) at runtime $\alpha_i$. The training points $x_i$ used for this are collected in a lexicon (dictionary) X. The cardinality of the lexicon X is usually limited in practice in order to keep storage time and/or computing time practical and/or limited.

For the present technical problem, namely to calculate the control signals (and/or target variables) $y_d$ in such a way (for example by determining the similarity in a high-dimensional, usually infinite-dimensional feature space (and/or Hilbert space), which is spanned by the transformation $\Phi$), that the quality measure is optimized (for example, $c_i \to 0$), algorithms for adaptive control calculation by kernel identification may be applied.

A KAF is implemented which learns the relationship $f$ between the input data (also: inputs) including the (for example, current) target motion state $\overline{x}_d$ and the control signal $y_d$, and the resulting result data (also: output) including the quality measure $c_i$(or $c_x$ and/or $c_y$):

$$c_i = f(\overline{x}_d, y_d), \tag{6}$$

inversely and suitable for prediction:

$$y_{d,next} = f_{KAF}(c_i, \overline{x}_d, y_d). \tag{7}$$

Alternatively, or additionally to the (for example, current) target motion state $\overline{x}_d$, the (for example, current) actual motion state $\overline{x}$ may be used (for example in equations (6) and (7) and in the implementation of the KAF described below).

It is possible to start without a special control signal, $y_d=0$ and the quality measure $c_i$ of the recorded images may be determined. In a next pass (and/or a repetition and/or iteration), the control signal (and/or target variable) $y_d$ may be changed so that the quality measure $c_i$ also changes. This change (for example, of the control signal $y_d$ and/or the quality measure $c_i$) forms the basis for the ML similarity analysis in the KAF. The procedure is similar to the ILC Method from FIG. 13, but the signal processing used is very different.

ML is used to predict new suitable control signals $y_d$ for example at runtime). Therefore, (for example for the kernel trick), data points $x_i$ must be formed in such a way that they include a time pattern (and/or history) of the target variables $y_d$ used in the state $\overline{x}_d$ and the associated error variables $c_i$. The kernel trick according to equation (3) may then be used to determine the similarity points defined in this way in the feature space $\mathcal{H}$.

The result of the kernel trick may be used to "query" new target variables $y_{d,next}$ with a KAF according to equation (7), so that these are as similar as possible to the data points with a future optimized quality measure (for example, $c_i \to 0$) in the feature space.

Since static effects do not contribute (and/or not only static effects contribute) to the quality measure (for example, $c_i$), it is important to train the KAF with time embedding (and/or the history) of the data in which not only the current time step is used. A longer time section (for example, several sampling steps and/or time embedding) of the signals (for example including quality measures, motion states and control signals) is combined to form a higher-dimension vectorial data point (for example, in the space SA designated with reference sign 902 in FIG. 9) with which the KAF is trained.

Discrete-time sampled signals $q[t]$, $c_i[t]$, . . . are available for implementation. In order for the KAF to be able to learn mapping that adequately takes into account the dynamic effects occurring on the system, for the construction of the data pairs $(x_i, x_j)$ used in the filter, it is essential to use, not only the variables of the current sampling step k, but also the time embedding over several time steps. For the technique, the data point $x_i[k]$(for example as a data point in the set 902 in FIG. 9) is constructed in the time step k as follows:

$$x_i[k] = \begin{pmatrix} c_i[k+r_c] \\ c_i[k+r_c-1] \\ \vdots \\ c_i[k] \\ c_i[k-1] \\ \vdots \\ c_i[k-T_c] \\ q[k] \\ \dot{q}[k] \\ \vdots \\ q[k-T_q] \\ \dot{q}[k-T_q] \\ \vdots \\ y_d[k] \\ \vdots \\ y_d[k-T_y] \end{pmatrix}. \tag{8}$$

Here, $r_c \in \mathbb{N}$ designates the prediction horizon (for example directed toward the future) and $T_c \in \mathbb{N}$, $T_q \in \mathbb{N}$ and $T_y \in \mathbb{N}$ designate the orders of the time embedding (for example directed toward the past) of the variables $c_i$, q, $\dot{q}$ or $y_d$.

In a particularly simple variant, the prediction horizon $r_c=1$ may be selected according to the next time step. According to other preferred variants, the prediction horizon $r_c>1$ is selected according to a plurality of time steps in a time series prediction.

Both the control signal $y_d$ and the associated quality measure $c_i$ are used to preprocess the data point $x_i[k]$. To provide the adaptive control system to advantageously suppress unknown disturbance variables d, it is furthermore necessary to include the motion state $$\overline{x} = \begin{bmatrix} q \\ \dot{q} \end{bmatrix}$$

of the system in the data point $x_i[k]$. This results in (8).

The data point $x_i[k]$ in equation (8) is usually queried in each time step k, wherein each step includes looking into the future (and/or "forward") by $r_c$ time steps.

The problem is solved with a KAF defined via the data according to equation (8), (for example, phase-by-phase and/or step-by-step).

In a first phase, no data is available and/or the lexicon is empty (X=Ø). A lexicon (and/or dictionary) X that is sufficiently informative for the beginning (for example for training the KAF) is created. To generate the first data points, the (for example, entire) X-ray device (also: imaging system) is moved to the desired positions $q_d(t)$ and a vanishing control signal is used for the compensation actuator system ($y_d(t)=0$) of the smart grid. During this time, the actual motion states $\overline{x}(t)$ and the associated achievable quality measure $c_i(t)$ of the X-ray recording (and/or imaging) are measured. Since the smart grid is not actuated, the quality measure is, as expected, poor ($c_i \gg 0$). The data points $x_i[k]$ for all sampling steps $\max(T_c, T_q, T_y) \le k \le T - r_c$ according to equation (8) are formed from the collected signal patterns of length T and added to the lexicon (and/or dictionary), $X[k]=X[k-1] \cup x_i[k]$, for example if the data points are sufficiently different. Appropriate methods for evaluating the informative value of potentially added data points with respect to the already existing lexicon (and/or dictionary) are known in KAF literature.

The lexicon (and/or dictionary) X may be expanded during the course of use (for example, of the X-ray device). In practice, an expansion of the lexicon (and/or dictionary) X may only be useful to a limited extent due to computing time and/or storage time and, when the limit is reached, old data points in the lexicon (and/or dictionary) X may be overwritten, Details of this are, for example, known.

In a second phase (and/or a next pass), the control signal is changed, namely by using the predictive capability of the KAF according to equation (7) in each sampling step $\max(T_c, T_q, T_y) \le k \le T - r_c$ with the aim of obtaining the best possible quality measure (for example $c_i=0$) when the next control signal (and/or the next target control variable) $y_d[k+1]$ is introduced, for example $$y_{d,predict}[k+1] = \sum_{i=1}^{|X|} \alpha_i \kappa(x_i[k], x_{query}[k]), \tag{9}$$

wherein the point "to be queried" $x_{query}[k]$(for example as a data point in the set 902 in FIG. 9) is constructed by $$x_{query}[k] = \begin{pmatrix} 0 \\ 0 \\ \vdots \\ c_i[k] \\ c_i[k-1] \\ \vdots \\ c_i[k-T_c] \\ q[k] \\ \dot{q}[k] \\ \vdots \\ q[k-T_q] \\ \dot{q}[k-T_q] \\ \vdots \\ y_d[k] \\ \vdots \\ y_d[k-T_y] \end{pmatrix}. \tag{10}$$

The data points $x_i[k]$ in equation (9) correspond to the entries in the lexicon (and/or dictionary) X.

Therefore, due to the zero entry in the first $r_c$ entries of the vector, the KAF predicts the value of the control signal $y_d$ (for example $y_d[k+1]$) that has the greatest possible similarity in the implicit feature space $\mathcal{H}$ to a point that represents the current motion state pattern of the X-ray device, the current smart grid compensation control signal pattern (and/or target variable curve) and the future optimum quality measure $c_i=0$ (and/or perfect artifact compensation).

In equation (10), the prediction horizon re is used to instruct the KAF to find data (for example control signals) in all $r_c$ future steps such that the quality measure (also: error measure) is $c_i=0$. If, for example, the prediction horizon were only $r_c=1$ step forward, control signals may be obtained so that the quality measure (also: error measure) $c_i$(for example, always) oscillates around the value 0. If, Alternatively, or additionally, a plurality of time steps (and/or $r_c>1$, and/or simultaneously) are set to $c_i=0$, the signal tends to be pushed into a stationary state.

Since the lexicon (and/or dictionary) X is initially filled with causally available data, the vector of equation (8) cannot be determined "all the way to the end T" on the basis of the collected signal patterns, but the determination is terminated at (and/or after) $r_c$ time steps. Alternatively, or additionally, a start is only possible when at least the embedding depth of data is available, as expressed in technically precise terms by the restriction to $\max(T_c, T_q, T_y) \le k \le T - r_c$ during the data collection.

Alternatively, or additionally, the KAF is trained with training sets including the data points $(x_i, c_i)$. Then, the trained KAF is used to ascertain estimated values $c_{est}$ as $c_{i,est}=\mathrm{KAF}(x_i)$ and determine a prediction quality as an MSE, $\Sigma_i(c_i-c_{i,est})^2$. Here, $c_{i,est}=\mathrm{KAF}(x_i)$ may refer to the evaluation of equation (7) and/or (9).

Thus, control signal values $y_d[k+1]$ that may be calculated at runtime are obtained by "asking" the KAF (which is, for example, continuing to learn) at each time step k which choice of control signal (and/or control variable) $y_d$ will in future optimize (or optimize as far as possible) the quality measure of the X-ray image. As a result of the fact that, using the new target variable curves (for example, for the motion state $\bar{x}_d$, the control signal $y_d$ and/or the quality measure $c_i$) will result in different values (for example, for the motion state $\bar{x}$ and/or the achieved quality measure $c_i$, that may also be referred to as image quality), the KAF is further trained analogously to the first (and/or) phase. Ultimately, this amounts to an online change to the lexicon (and/or dictionary) X and/or the weighting factors $\alpha_i$(for example, in equation (5)).

The procedure in the second phase (and/or the next run) and the obtaining of the control signal values that may be calculated at runtime may be iterated.

Alternatively, or additionally, the changes in the control signal and the quality measure may be iterated and, with a correctly set KAF, the quality measure (and/or the image quality) may gradually develop further and further in the direction of optimization (for example, $c_i \to 0$), for example for all target motion states (and/or target gantry movement patterns) $q_d(t)$ and/or $\bar{x}_d(t)$.

Furthermore, Alternatively, or additionally, a new target variable may be queried from the KAF and applied, thereby generating a new data point that may or may not be included in the KAF. The KAF may then be queried again and the subsequent steps repeated.

Depending on the properties of the quality measure, different types of KAF may be used. For example, for a proof-of-concept, the original KAF (for example, as disclosed in [10]), may be used, for example as a starting point. The original KAF includes a kernel variant of the well-known "recursive least-squares" filter.

If the quality measure (and/or the image quality, for example, $c_i$) deteriorates significantly over the lifetime of the device (and/or the runtime of the X-ray device) (for example, due to ageing effects), a KAF may be used that has a built-in forgetting mechanism (for example, a KAF with a forgetting mechanism is known.

Alternatively, or additionally, in practice, the memory limitation and/or the real-time capability, for example the limited computing time for each iteration, plays a role. Therefore, the number of points in the lexicon (and/or the set) X is restricted to an appropriate cardinality. KAFs whose performance is limited in exchange for computing time could advantageously be used for this purpose. Such a KAF is, for example, described in known references.

To ensure that the KAF functions as planned (and/or desired), it is usually necessary to set hyperparameters during development that influence the learning policy of the selected algorithm. These for example include the parameters of the kernel κ, σ, the prediction horizon $r_c$, and/or the orders $T_c$, $T_q$, $T_y$ of the time embedding.

If expected signal properties for the kernel function κ are known a priori (for example, a predetermined and/or certain number of them) (for example, a periodicity), the expected signal properties may be coded into the KAF by the (for example suitable) choice of a corresponding kernel. If no expected signal property is known (and/or no suitable KAF for an expected signal property is known), the Gaussian kernel of the equation (4) is selected (for example, generically).

The variant (and/or the scalar) $\sigma>0$ in equation (4) is for example chosen approximately in the order of magnitude of the expected deviations $\|x_i-x_j\|$ so that the kernel is not too narrow, no overfitting of the training points occurs and/or a (for example, limiting and/or certain) generalization is possible.

The prediction horizon $r_c$ may (for example usually) be set to one (1). However, if the computing time is so slow that the KAF cannot be calculated in each control cycle, a multi-step prediction (and a prediction horizon $r_c>1$) is possible, for example, $r_c=10$.

The time embedding is selected as large as necessary and/or as small as possible. A suitable value for the time embedding may, for example, be ascertained experimentally. The experiment may be started with small orders $T_c$, $T_q$, $T_y$ of the time embeddings. One or more values of the orders $T_c$, $T_q$, $T_y$ is advantageously only increased if the results achieved (for example, quality measures) are not satisfactory. Values (for example, approximately) of $T_c=5$, $T_q=2$, $T_y=5$ may be used as a starting point for the technique of compensating the X-ray grid shadow.

Standard KAFs make it possible (for example, only) to learn and/or predict the scalar relationships in equations (5), (7) and (9). In order to tilt the smart grid (and/or high aspect X-ray grid) in such a way that the migration of the X-ray beam is fully compensated, (for example, however,) m (generally at least m=2) degrees of freedom are necessary. Therefore, in practice, m KAFs according to equation (9) run in parallel, wherein each of the KAFs generate the control signal (and/or the control variable) of a single degree of freedom. The generation of a control signal for each degree of freedom may be referred to as multi-scale control.

For training and/or for inference, the multi-dimensional control signal $y_d$ in equation (8) or (10) may (for example, however nevertheless) be used, together with the quality measure $c_i$, which reports back the image quality overall. If the learning algorithms do not work in this setup, the two KAFs may alternatively be filled separately in the x-direction or y-direction of the X-ray grid with data that describes the direct correlation in the respective direction. This may be done analogously to the above-describe procedure, wherein (for example, however), in each step, the respective quality measure that only measures in one coordinate direction (for example, $c_x$ or $c_y$) is used instead of the overall quality measure $c_i$.

The technique differs fundamentally from conventional signal processing methods or control engineering methods (for example those cited in the prior art).

Kernel adaptive filters per se have been the subject of research for several years. However, the fields of application of KAFs are not described. In the technique, the KAF is used (for example as a function approximator) in order to ultimately generate an adaptive control signal.

In the sense of the technique, control includes "feedforward control". Alternatively, or additionally, the KAF depends on the output achieved (for example, the quality measure). Furthermore, Alternatively, or additionally, a control signal (or feedforward control) is generated, which is tracked by a subordinate regulator, for example the compensation actuator system.

The KAF may act in a similar way to system inversion, wherein "system" may be understood to mean the entire chain starting from the control signal of the compensation actuator system of the smart grid up to the final relevant variable, the quality measure (and/or the image quality, for example, $c_i$). Although adaptive system inversion has been the subject of research in control engineering for decades, mainly using NNs, no applications for improving (for example, X-ray) image quality are known.

Figure 14:
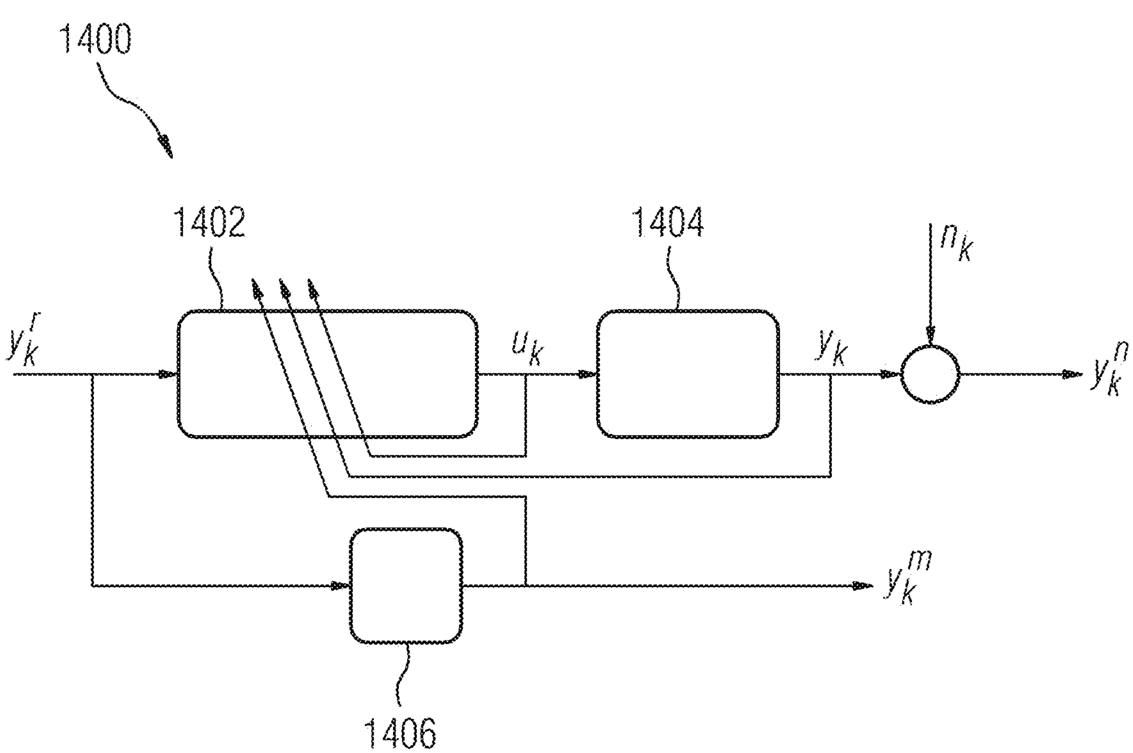
FIG. 14 depicts a KAF control system from the prior art, which works with a reference model and without (for example unknown) disturbance variables.

A KAF is used to describe an inverse control system in the context of MRAC (model reference adaptive control). FIG. 14 is a schematic view of the architecture 1400 of the KAF control system from [6]. Herein, a model M at reference sign 1406 generates the target variables $$y_k^m$$

based on the reference variable $$y_k^r.$$

The output of the KAF 1402 is $u_k$, i.e. the control of the system (plant) 1404.

The method differs from the known methods in that the reference variable used for the quality measure (for example, $c_i$) is the (for example optimum) value 0. Furthermore, the method does not use a reference model (and/or M=0).

Further control variables intervene in the system, namely the target motion states (and/or motion variables) of the pivotable arm (and/or the gantry) $q_d$ (and/or $\overline{x}_d$). Furthermore, the technique therefore does not only have additive disturbance variables at the output. The greatest obvious difference is that, an imaging method (for example X-ray) is used, therefore, the controlled system ("plant") is technically much more comprehensive and cannot be described with a reference model M. Instead, the KAF must have a better generalization capability in order to extrapolate new control signals based on the data points of the lexicon (and/or dictionary) X. This use of the KAF is referred to as kernel adaptive identification feedforward extrapolation.

In a further embodiment, a class of AI (artificial intelligence) methods, for example reinforcement learning (RL) is used to determine the control signal (also: control variable) and/or as a function approximator.

Figure 10:
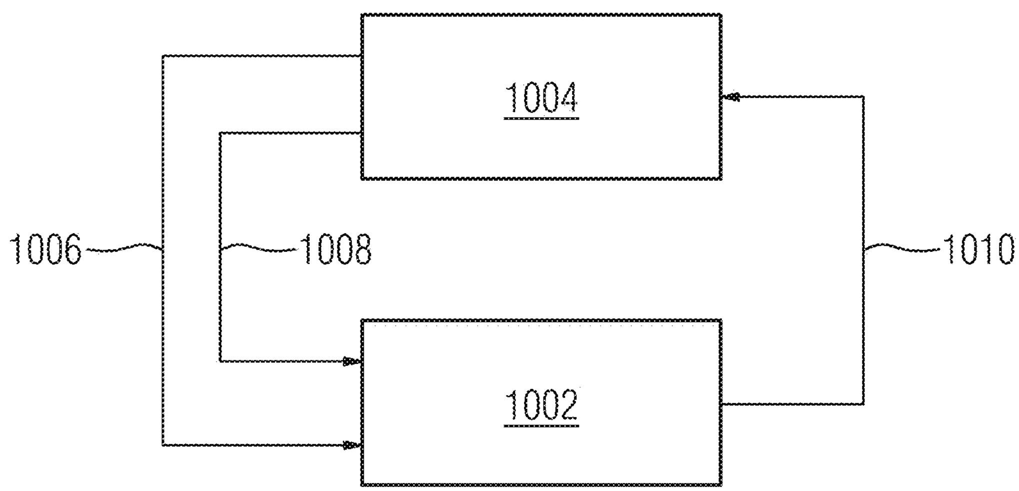
FIGS. 10, 11 and 12 depict embodiments of an agent, that is used as a function approximator when using RL. 0

RL is known in principle. FIG. 10 is a schematic sketch of the basic idea of RL, according to which learning control is configured as an agent 1002 whose actions 1010 have an influence on the environment 1004 of the agent 1002, the quality of which may in turn be measured by a reward signal 1008 and the state 1006 of which changes due to the actions 1010 of the agent 1002. The aim of the learning agent 1002 is to learn a policy iteratively so that the rewards 1008 expected in the future are maximized and/or therefore the agent 1002 behaves optimally.

In RL, the agent 1002 in FIG. 10 embodies the function approximator (for example as a part, and/or function, of the control signal determining unit 206). The environment 1004 may embody all further components of the computing apparatus 200 and/or the system including the X-ray device. The quality measure (for example, $c_i$, $c_x$ and/or $c_y$) may be configured by a reward signal 1008 (and/or perceived as a reward signal 1008).

In the sense of RL, FIG. 6 may be regarded as an agent at reference sign 604 and the environment (all further reference signs).

Figure 11:
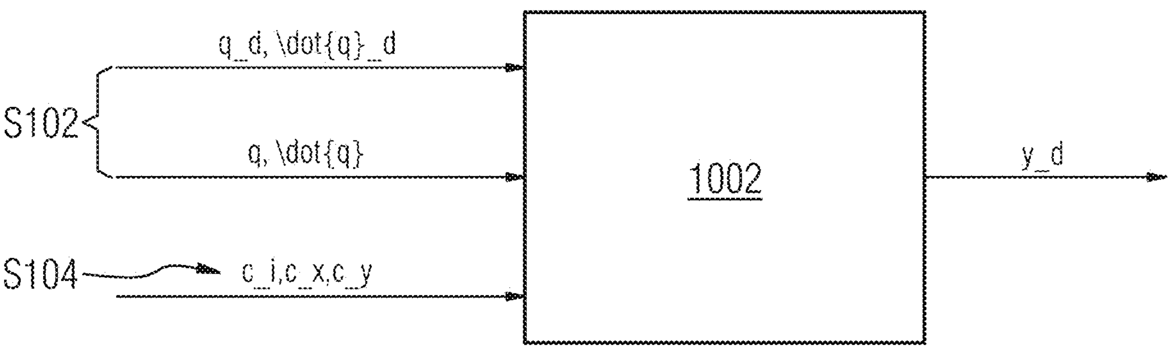
Figure 12:
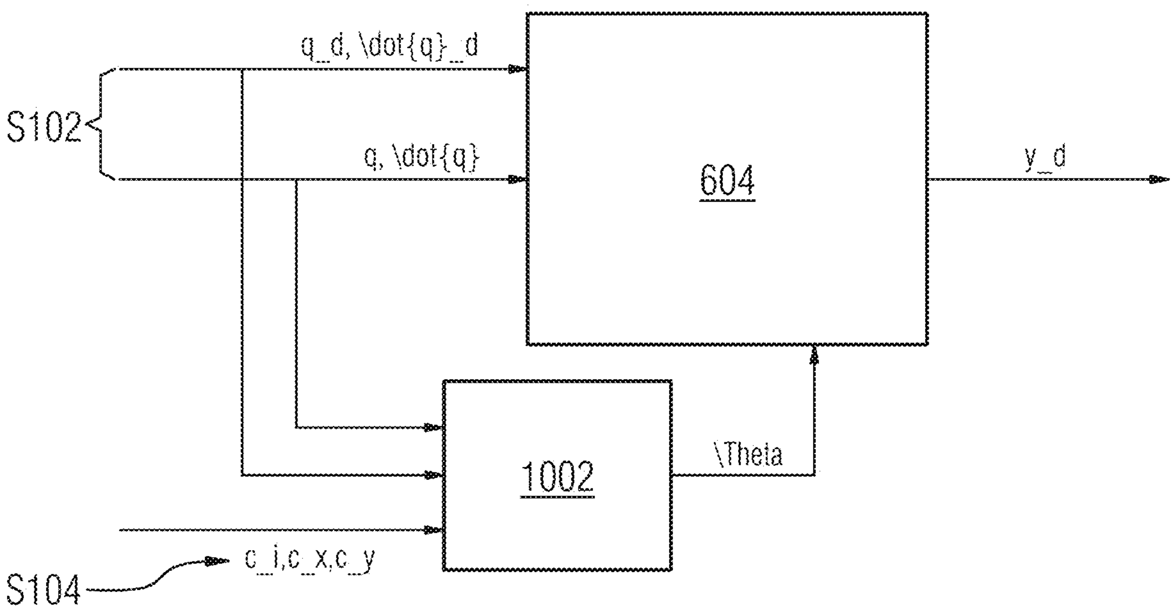

In the context of RL, the determination 604 of the control signal in FIG. 6 may be replaced by a policy of an agent 1002 according to FIG. 11, or according to FIG. 12, a parameter Θ of a control law may be perceived as a possible action space of an agent 1002.

From the diverse class of RL algorithms, the most suitable methods for the characteristics of the application are selected. For compensation of an X-ray grid shadow, this is restricted as follows. The state space (for example, motion state space) is continuous. The action space may advantageously also be considered to be continuous in order to provide a precise compensation actuator system (for example, in contrast to RL with discrete actions).

Off-policy and/or on-policy learning may be used. Since this is an iterative roll-out-based learning method, Alternatively, or additionally, the class of "policy search" and/or "actor-critic" algorithms may be advantageous. Alternatively, or additionally, value-based algorithms (for example, least square policy iteration, LSPI) may be disadvantageous with respect to framework conditions regarding learning time and/or computing time for inference.

In a prototypical implementation of RL, it is advisable to start from the prior art, for application to the active compensation of the X-ray grid shadow.

The applicability of the learning methods of all embodiments (for example RL) is due to the fact that the control signal generated by the learning control may be (for example, relatively) easily checked for plausibility and (for example when necessary) further restricted (for example, to a permissible setting range for the compensation actuators).

Since the X-ray grid (and/or raster) has a predetermined height, in addition to widening of the bars, a tilted X-ray beam also leads to shifting of the slats (also: bars) on the X-ray image.

The shifting of the slats relative to a calibration image may be determined (and/or measured) by systematically shifting the initial calibration image in all directions in small steps (for example with a step length much smaller than a pixel size) with the aid of an interpolation method and measuring the deviation (for example, the standard deviation of the difference between the shifted image and the current projection). The magnitude of the shift vector that minimizes the difference may include the quality measure (and/or the return variable, for example, $c_i$, $c_x$ and/or $c_y$) (for example for each shift direction x or Y).

An alternative method includes an analysis of 2D Fourier transform images.

Figure 15:
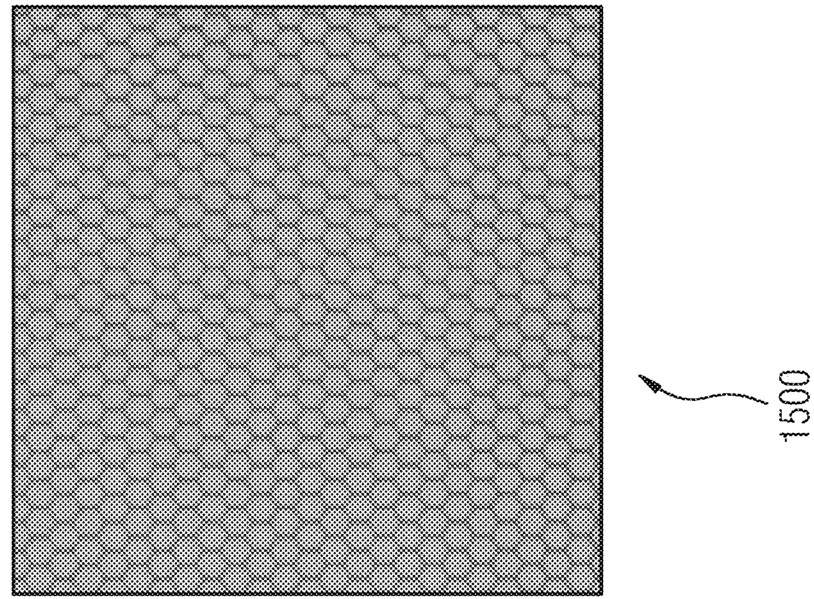
FIG. 15 depicts an X-ray image of a honeycomb X-ray grid, for example without compensation according to an embodiment.

FIG. 15 shows by way of example a recorded X-ray image 1500 of a honeycomb X-ray grid (also: raster image), for example without compensation (and/or correction).

Figure 16:
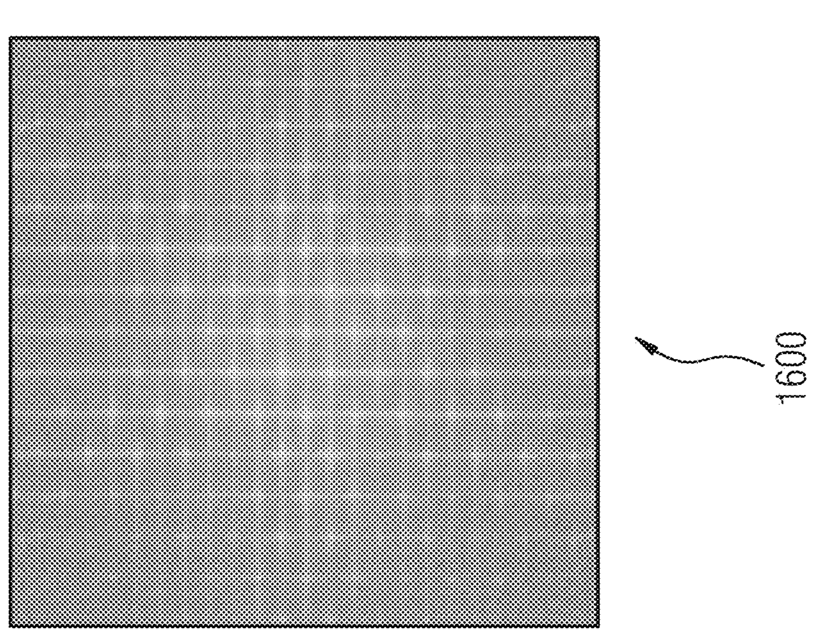
FIG. 16 depicts a 2D FFT image of an X-ray image that was recorded with an X-ray grid on the detector according to an embodiment.

FIG. 16 shows a 2D Fourier-transformed (for example FFT-transformed) image 1600 of an X-ray image recorded with an X-ray grid.

The more local maxima (and/or patterns) of the amplitudes are visible in the FFT image, the more disruptive periodic structures (for example inclined slats of a smart grid) may be present in the X-ray image. The sum of the amplitudes of the local maxima may be captured. The sum of the amplitudes may determine the quality measure (and/or the return value, for example, $c_i$) and/or be (for example, inversely) proportional to the quality measure.

The FFT image may look similar with and/or without patients in the X-ray beam (and/or between the X-ray source and the detector), since the FFT acts on regular and/or periodic signal components. A patient in the X-ray beam usually leads to irregular signal components and/or frequency components and is (for example, only) smoothed and/or visible in the FFT image. On the other hand, the X-ray grid usually contributes to a regular and/or periodic signal component.

The FFT image is based on the fact that each curve and/or each 2D image may be broken down into a unique sum of fundamental waves with different frequencies and amplitudes, as shown in FIG. 16 by way of example. This shows the amplitudes. The brighter the FFT image (for example, in FIG. 16), the greater the amplitude of the associated fundamental wave.

The low-frequency fundamental waves are located in the center point of the FFT image. The closer to the edge, the higher the frequency of the fundamental wave. The direction reflects the orientation of the fundamental wave.

Figures 17A, 17B, 17C:
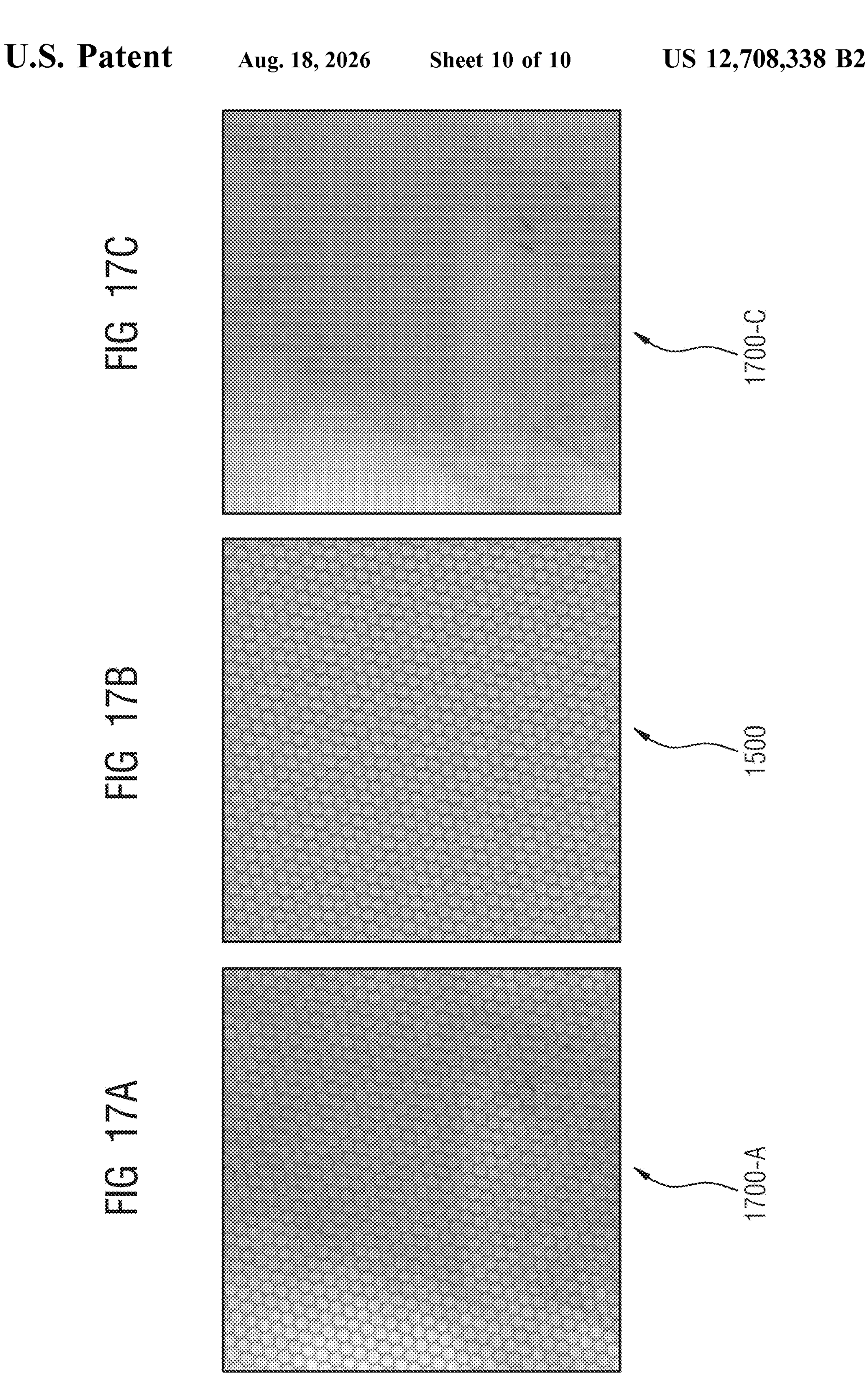
FIGS. 17A, 17B and 17C depict an example of the subtraction of a calibration image from a recorded X-ray image in order to calculate out the X-ray grid from the output X-ray image according to an embodiment.

FIGS. 17A, 17B and 17C show by way of example a subtraction (and/or division) of a calibration image. A calibration image 1500 of the X-ray grid in FIG. 17B is deducted (and/or subtracted and/or divided) from the X-ray image 1700-A of a patient recorded with the X-ray grid in FIG. 17A, so that the subtraction image 1700-C shown in FIG. 17C (and/or division image, which may also be referred to as a useful medical image) showing structures of the patient is produced.

If a calibration image (and/or pure image) of the X-ray grid (and/or raster) without a patient is available that which matches the recorded X-ray image (for example with a patient) (for example, in size, orientation and type of X-ray grid), the recorded X-ray image (for example with a patient) and the calibration image may be subtracted from one another (and/or divided by one another). This means the X-ray grid (and/or raster) is omitted from the subtraction image (and/or division image).

The subtraction principle (and/or division principle) of the X-ray images may be considered to be analogous to digital subtraction angiography in which only vessels are to be depicted and the anatomy is "subtracted away" (and/or "divided away") by subtraction (and/or division) with a pure anatomical image.

The more deviations from the periodicity (for example, due to tilting of the X-ray grid and/or raster) visible in the FFT image, the more the peaks in the Fourier image disappear and it becomes more and more homogeneous—there are fewer and fewer characteristic frequencies. This change may be learned in a measurement with the shift vector (and/or quality measure, for example, $c_i$) with the aid of phantoms and later applied inversely.

Thus, analyzing the periodicity of the FFT image provides the extent of artifacts to be determined and/or compensated (also: calculated out).

In a further embodiment, end-to-end learning is applied to learn the control signals of the compensation actuator system of the smart grid and/or the movement of the pivotable arm (and/or gantry movement). In end-to-end learning, all steps between the input and final result are learned independently by AI.

For example, it is known to generate a control for a robot arm so that the robot places books on a shelf directly from raw images provided by a camera directed at the scene. The robot thus observes itself and thereby learns the necessary movements for obtaining a desired camera image.

Transferred to X-ray imaging and the control of the compensation actuator system of the smart grid, in FIG. 7, the determination processes for the control signal and quality measure shown separately at reference sign 604 or 616 may be replaced by end-to-end learning at reference sign 605 (for example as a function approximator).

Furthermore, a possible input of reference images for end-to-end learning at reference sign 605 is shown at reference sign 618 in FIG. 7.

A deep RL method may be used to implement the end-to-end learning block 605. Herein, in addition to a RL policy $\pi$ for calculating the control signals, the required rewards are calculated directly from the recorded X-ray images (also: for example useful medical images) 612 by training a deep CNN classifier by RL. The recorded (also: obtained in use) X-ray images 612 are compared with reference images 618 (and/or labeled).

Alternatively, or additionally, as shown schematically in FIG. 8 at reference sign 620, the recorded X-ray images 612 may be labeled with an evaluation by one or more experts (for example a radiologist), so that the policy $\pi$ is iteratively improved with respect to the rewards calculated in this way. As a result, the control of the compensation actuator system will gradually function in such a way that X-ray images are obtained that have fewer artifacts overall.

As shown by way of example in FIG. 8, end-to-end learning may be generalized in such a way that even the motion state data (and/or system motion) is generated from the desired X-ray images.

End-to-end learning of the compensation of the X-ray grid shadow offers considerable advantages. Alternatively, or additionally, end-to-end learning may additionally use a surround-view camera that monitors a relative position of the X-ray source and the detector (and/or the C-arm) from the outside and (for example, additionally) generates ground truth for the learning method (for example with respect to the motion state data and/or the assigned quality measure, for example when the control signal disappears).

Alternatively, or additionally, the only factor relevant for end-to-end learning based on the useful medical image may be the appearance of an image with artifacts in comparison to one without artifacts and learning the relationship with the positioning of the pivotable arm (and/or the actuator system) that generates the artifacts. For example, other influencing factors may be omitted. Alternatively, or additionally, the control signals generated in this way may be combined in a subsequent (and/or second) step with a monitoring function that uses conventional methods, for example, based on a surround-view camera, to monitor what is happening in the room and/or the environment.

The technique is advantageously agnostic with respect to the specific mechanical structure and the physical reasons (for example, shadowing and/or focus migration) that result in an impairment of X-ray image quality since the quality measure may be determined (and/or measured) directly in the resulting X-ray image and the compensation is (for example exclusively) determined (and/or calculated) in a data-driven manner. Thus, the technique may be easily transferred to new types of imaging (for example X-ray) systems, new system versions and/or system variants, in contrast to conventional model-based methods, which require development outlay in each case.

In conventional methods, statically approached positions could be made useable since, only in this case is difference calculation possible by calibration images or modeling is otherwise too complex and/or cannot be calculated at run-time. The technique provides (for example, in principle) compensation for dynamic travel.

Since the technique achieves high-precision actuation and provides compensation of highly non-linear and/or unknown (and/or hard-to-measure) effects, higher mechanical deformation than is conventionally the case may be tolerated. This means the pivotable arm (and/or the gantry) does not have to be made even more structurally stable; on the contrary it may even be made less rigid.

This provides material savings in the design, since many requirements, for example, with respect to gears and/or bearings, which were previously necessary to prevent mechanical vibrations from occurring in the first place, may be reduced.

In addition, variations in series production could be better tolerated when using the technique than with a conventional model-based approach based on a single fixed model.

The attachment of the detector to the pivotable arm (for example C-arm) in a tilted and/or inclined manner is conventionally not tolerable. The technique provides compensation, for example by the compensation actuator system, so that production waste may be reduced.

From the perspective of achievable performance, the technique has the advantage that learning mechanisms (for example for the function approximator) may continue to be active during the life cycle of the X-ray device in order to counteract (for example automatically) slowly changing processes that impair imaging. For example, poorer or different dynamics may occur in the mechatronic drive train due to wear.

The technique may also be used if the compensation actuator system is attached to the emitter side to compensate mechanical inadequacies on the emitter side.

A (for example, further) advantage of the ILC method is acausal filtering which is possible due to the iterative learning approach. Thus, precision control of the compensation actuator system may be learned in such a way that it so-to-speak intervenes even before the effects due to the dynamics would occur later. This is possible because the filters L and Q of the ILC method may even be acausal, which is for example an advantage compared to an online method. The reason for this that ILC changes the control signal of the next iteration by calculating between the iterations and, at this time, the signal patterns of the previous iteration are completely available. It is therefore possible to filter forward or backward or acausally.

A (for example, further) advantage of kernel-trick-based KAF is, that (for example, also) strongly non-linear effects may be learned. Alternatively, or additionally, the KAF is online-capable, for example learning not only between executions of the movement, but also during executions thereof.

One (for example, further) advantage of RL is that it is more general than ILC (for example, ILC may be perceived as a relatively simple RL strategy for episodic settings). RL has a higher computational effort, a better generalization capability, and/or may also be applicable if the prerequisites for ILC (for example, repetitive execution of movements and repeatable disturbance variable patterns) do not apply.

The technique is for example evident when a mass (for example, 50 kg) is attached to the detector that increases the deflection of the pivotable arm (for example C-arm), and the image quality then nevertheless improves again after a few runs.

Unless explicitly described, individual embodiments or individual aspects and features thereof described with reference to the drawings may be combined or interchanged with one another without restricting or broadening the scope of invention described if such a combination or interchange is advisable and is within the spirit of the present invention. Where applicable, advantages described with respect to a certain embodiment of the present invention or with respect to a certain figure are also advantages of other embodiments of the present invention.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that the dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A computer-implemented method for controlling a compensation actuator system for compensating a shadow of an X-ray scattered radiation absorption grid in an X-ray image recorded with a pivotably mounted X-ray device, comprising:

- receiving motion state data indicative of a motion state of an X-ray device, wherein the X-ray device is mounted on a pivotable arm, and wherein the motion state is assigned to a time of recording of an X-ray image by the X-ray device;
- determining a quality measure of the X-ray image with respect to a shadow of an X-ray scattered radiation absorption grid, that is arranged on a detector of the X-ray device;
- determining a control signal for the compensation actuator system for adjusting a position of the X-ray scattered radiation absorption grid depending on the received motion state data and depending on the determined quality measure, wherein determining the control signal comprises optimizing the quality measure; and
- outputting the determined control signal to the compensation actuator system in order to compensate the shadow of the X-ray scattered radiation absorption grid.

2. The method of claim 1, wherein the pivotable arm comprises a C-arm.

3. The method of claim 1, wherein the position of the X-ray scattered radiation absorption grid arranged on the detector comprises a position in a detector plane and/or in a plane perpendicular to a focal direction of an X-ray source of the X-ray device.

4. The method of claim 1, wherein the motion state comprises an orientation in space and/or a speed of position adjustment of the pivotable arm and/or the X-ray device.

5. The method of claim 1, wherein the received motion state data comprises target motion state data and/or actual motion state data.

6. The method of claim 1, wherein compensating the shadow comprises tilting and/or shifting the X-ray scattered radiation absorption grid and/or tilting and/or shifting an X-ray source.

7. The method of claim 1, wherein the compensation actuator system comprises two compensation actuators, and wherein a first compensation actuator is configured to tilt and/or shift the X-ray scattered radiation absorption grid along a first direction of a detector plane, and wherein a second compensation actuator is configured to tilt and/or shift the X-ray scattered radiation absorption grid along a second direction of a detector plane.

8. The method of claim 1, further comprising:

- outputting the recorded X-ray image comprising compensating in real time, the shadow of the X-ray scattered radiation absorption grid.

9. The method of claim 1, wherein the quality measure comprises a quality measure for each direction.

10. The method of claim 1, wherein determining the quality measure comprises a comparison with one or more datasets in a lexicon, wherein each dataset in the lexicon comprises a motion state, a quality measure and a control signal to compensate the shadow of the X-ray scattered radiation absorption grid.

11. The method of claim 10, wherein each dataset further comprises a temporal sequence of motion states, quality measures and optional control signals.

12. The method of claim 1, wherein determining the quality measure comprises evaluating contrasts in a Fourier-transformed X-ray image.

13. The method of claim 1, wherein at least determining the quality measure of the X-ray image and determining the control signal for the compensation actuator system are carried out iteratively until the determined quality measure lies within a predetermined value range.

14. The method of claim 1, wherein determining a control signal for the compensation actuator system comprises at least one of machine learning, reinforcement learning, iterative learning control, kernel adaptive identification feedforward extrapolation, and/or end-to-end learning.

15. A computing apparatus for controlling a compensation actuator system for compensating a shadow of an X-ray scattered radiation absorption grid in an X-ray image recorded with a pivotably mounted X-ray device, the computer apparatus comprising:

- a receiving interface configured to receive motion state data indicative of a motion state of an X-ray device, wherein the X-ray device is mounted on a pivotable arm, and wherein the motion state is assigned to a time of recording of an X-ray image by the X-ray device;
- a quality measure determining unit configured to determine a quality measure of the X-ray image with respect to a shadow of an X-ray scattered radiation absorption grid, which is arranged on a detector of the X-ray device;
- a control signal determining unit configured to determine a control signal for a compensation actuator system for adjusting a position of the X-ray scattered radiation absorption grid depending on the received motion state data and depending on the determined quality measure, wherein the determining of the control signal comprises optimizing the quality measure; and a control signal output interface configured to output the determined control signal to the compensation actuator system in order to compensate the shadow of the X-ray scattered radiation absorption grid.

16. A non-transitory computer implemented storage medium that stores machine-readable instructions executable by at least one processor for controlling a compensation actuator system for compensating a shadow of an X-ray scattered radiation absorption grid in an X-ray image recorded with a pivotably mounted X-ray device, the machine-readable instructions comprising:

receiving motion state data indicative of a motion state of an X-ray device, wherein the X-ray device is mounted on a pivotable arm, and wherein the motion state is assigned to a time of recording of an X-ray image by the X-ray device;

determining a quality measure of the X-ray image with respect to a shadow of an X-ray scattered radiation absorption grid, that is arranged on a detector of the X-ray device;

determining a control signal for the compensation actuator system for adjusting a position of the X-ray scattered radiation absorption grid depending on the received motion state data and depending on the determined quality measure, wherein determining the control signal comprises optimizing the quality measure; and outputting the determined control signal to the compensation actuator system in order to compensate the shadow of the X-ray scattered radiation absorption grid.

* * * * *